US011792384B2

(12) United States Patent
Furst et al.

(10) Patent No.: US 11,792,384 B2
(45) Date of Patent: Oct. 17, 2023

(54) PROCESSING COLOR INFORMATION FOR INTRAORAL SCANS

(71) Applicant: Align Technology, Inc., San Jose, CA (US)

(72) Inventors: Gilad Furst, Petach Tikva (IL); Tal Verker, Ofra (IL); Ofer Saphier, Rechovot (IL)

(73) Assignee: Align Technology, Inc., San Jose, CA (US)

( * ) Notice: Subject to any disclaimer, the term of this patent is extended or adjusted under 35 U.S.C. 154(b) by 525 days.

(21) Appl. No.: 16/890,972

(22) Filed: Jun. 2, 2020

(65) Prior Publication Data

US 2020/0296352 A1 Sep. 17, 2020

Related U.S. Application Data

(63) Continuation of application No. 15/953,268, filed on Apr. 13, 2018, now Pat. No. 10,708,574.
(Continued)

(51) Int. Cl.
*H04N 13/257* (2018.01)
*G02B 27/10* (2006.01)
(Continued)

(52) U.S. Cl.
CPC ....... *H04N 13/257* (2018.05); *A61B 1/00006* (2013.01); *A61B 1/00096* (2013.01);
(Continued)

(58) Field of Classification Search
USPC .............. 382/154, 162; 348/45, 53; 356/601
See application file for complete search history.

(56) References Cited

U.S. PATENT DOCUMENTS 6,384,917 B1 * 5/2002 Fradkin .................... G01J 3/51
356/402
6,697,164 B1 2/2004 Babayoff et al.
(Continued)

FOREIGN PATENT DOCUMENTS

DE 102005043627 A1 3/2007
EP 2799032 A1 11/2014
WO 2012083967 A1 6/2012

OTHER PUBLICATIONS

Liu et al., Study of Color Matching System for Porcelain Teeth, 2013 IEEE 978-1-4673-5997-3/13, pp. 310-314. (Year: 2013).*
(Continued)

*Primary Examiner* — Ishrat I Sherali
(74) *Attorney, Agent, or Firm* — Lowenstein Sandler LLP

(57) ABSTRACT

A method includes receiving scan data of a tooth during a first mode of operation, the scan data of the tooth having been generated by an intraoral scanner. The method includes invoking a second mode of operation and presenting, in a GUI, an image of the tooth. The method includes presenting, in the GUI, indications of a plurality of color zones of the tooth, the indications comprising, for at least one color zone of the plurality of color zones, an indication that insufficient color information has been received, wherein each color zone represents a separate region of the tooth for which an approximately uniform color is to be used. The method includes categorizing, for one or more color zones of the plurality of color zones for which sufficient color information has been received, each of the one or more color zones according to a color pallet used for dental prosthetics.

25 Claims, 13 Drawing Sheets

Related U.S. Application Data

(60) Provisional application No. 62/520,417, filed on Jun. 15, 2017.

(51) Int. Cl.

| | | |
|---|---|---|
| *G02B 23/24* | (2006.01) | |
| *A61B 1/06* | (2006.01) | |
| *A61B 1/24* | (2006.01) | |
| *A61B 1/00* | (2006.01) | |
| *A61B 5/00* | (2006.01) | |
| *A61C 9/00* | (2006.01) | |
| *A61B 1/247* | (2006.01) | |
| *A61B 1/07* | (2006.01) | |
| *G01J 3/46* | (2006.01) | |
| *A61B 1/04* | (2006.01) | |
| *H04N 23/55* | (2023.01) | |
| *H04N 23/56* | (2023.01) | |
| *H04N 23/74* | (2023.01) | |
| *H04N 13/00* | (2018.01) | |
| *A61C 1/08* | (2006.01) | |
| *H04N 23/10* | (2023.01) | |
| *H04N 23/50* | (2023.01) | |

(52) U.S. Cl.
CPC .......... *A61B 1/00172* (2013.01); *A61B 1/043* (2013.01); *A61B 1/063* (2013.01); *A61B 1/0638* (2013.01); *A61B 1/0669* (2013.01); *A61B 1/07* (2013.01); *A61B 1/24* (2013.01); *A61B 1/247* (2013.01); *A61B 5/0073* (2013.01); *A61B 5/0088* (2013.01); *A61C 9/006* (2013.01); *G01J 3/46* (2013.01); *G02B 23/2446* (2013.01); *G02B 27/1013* (2013.01); *H04N 23/55* (2023.01); *H04N 23/56* (2023.01); *H04N 23/74* (2023.01); *A61B 5/0071* (2013.01); *A61C 1/088* (2013.01); *H04N 23/10* (2023.01); *H04N 23/555* (2023.01); *H04N 2013/0077* (2013.01); *H04N 2013/0081* (2013.01)

(56) References Cited

U.S. PATENT DOCUMENTS

| | | | |
|---|---|---|---|
| 7,064,830 B2 * | 6/2006 | Giorgianni | G01J 3/50 356/402 |
| 7,092,107 B2 | 8/2006 | Babayoff et al. | |
| 7,319,529 B2 | 1/2008 | Babayoff | |
| 8,310,683 B2 | 11/2012 | Babayoff et al. | |
| 8,363,228 B2 | 1/2013 | Babayoff | |
| 8,577,212 B2 | 11/2013 | Thiel | |
| 8,878,905 B2 | 11/2014 | Fisker et al. | |
| 9,261,358 B2 | 2/2016 | Atiya et al. | |
| 9,752,867 B2 | 9/2017 | Atiya et al. | |
| 9,956,061 B2 | 5/2018 | Moalem | |
| 10,206,558 B2 | 2/2019 | Pfeiffer et al. | |
| 10,708,574 B2 * | 7/2020 | Furst | G01J 5/047 |
| 2006/0001739 A1 * | 1/2006 | Babayoff | A61B 1/0646 348/E13.005 |
| 2009/0079993 A1 | 3/2009 | Yatagai et al. | |
| 2009/0133260 A1 * | 5/2009 | Durbin | A61C 13/082 29/896.11 |
| 2011/0221879 A1 | 9/2011 | Schmidt | |
| 2014/0022356 A1 * | 1/2014 | Fisker | A61B 5/4542 348/47 |
| 2014/0119622 A1 | 5/2014 | Babayoff | |
| 2015/0022824 A1 | 1/2015 | Babayoff | |
| 2016/0051345 A1 * | 2/2016 | Levin | A61C 9/0053 433/29 |
| 2018/0028063 A1 | 2/2018 | Elbaz et al. | |
| 2019/0230336 A1 | 7/2019 | Babayoff | |

OTHER PUBLICATIONS

"Digital Red, Green and Blue Color Light Sensor with IR Blocking Filter," IntersilTM Datasheet, Jan. 15, 2016, 17 pages.

Ramanathan, G., "Colorimeter vs. Spectrophotometer: Knowing the Differences Among Color Measurement Technologies" Hunter Lab, Mar. 26, 2016, 8 pages.

\* cited by examiner

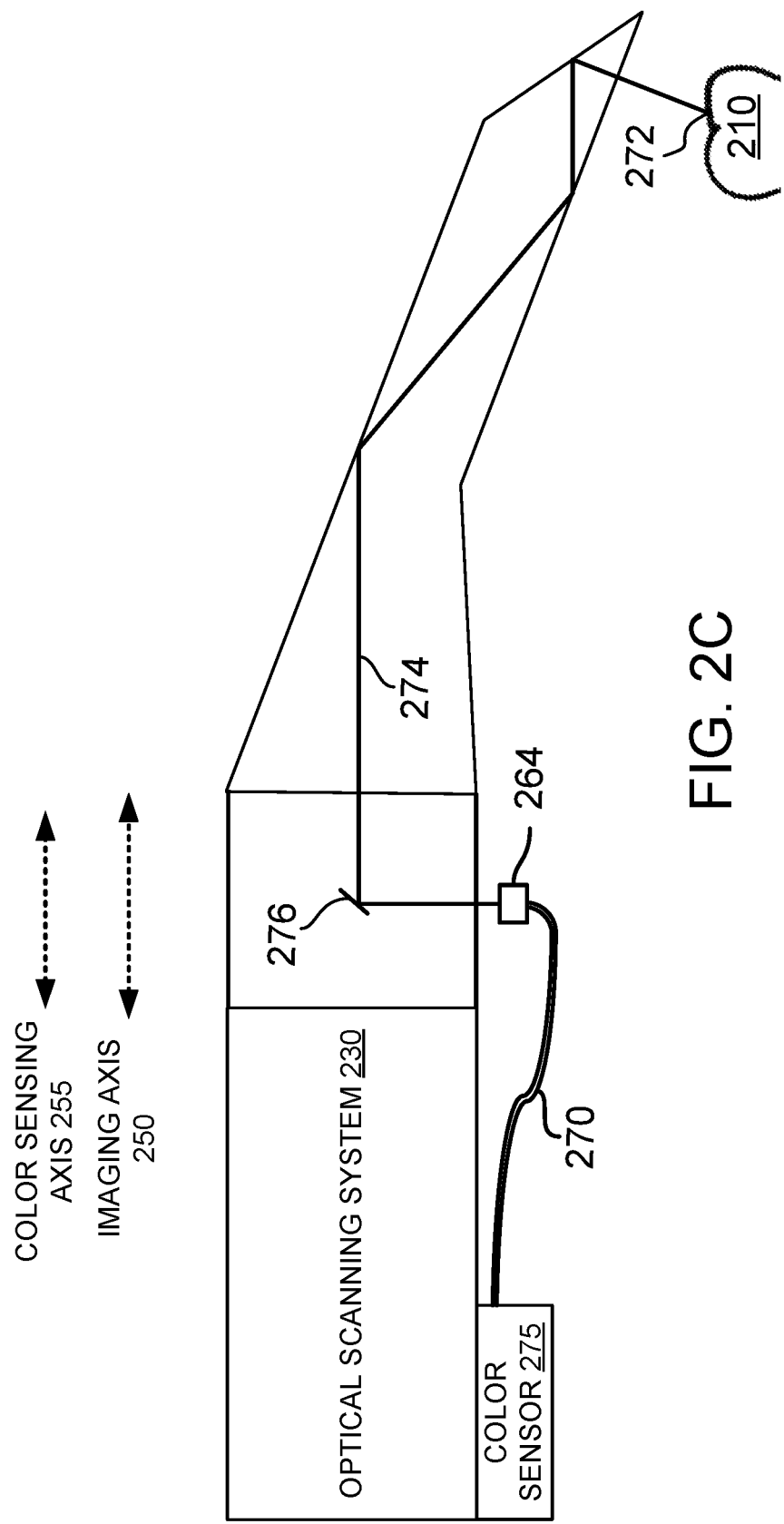

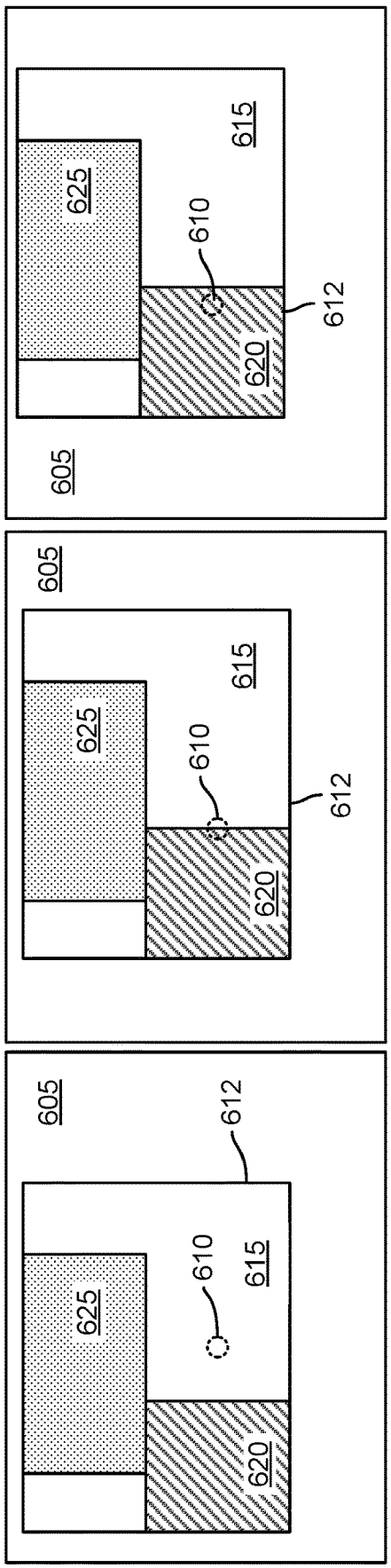
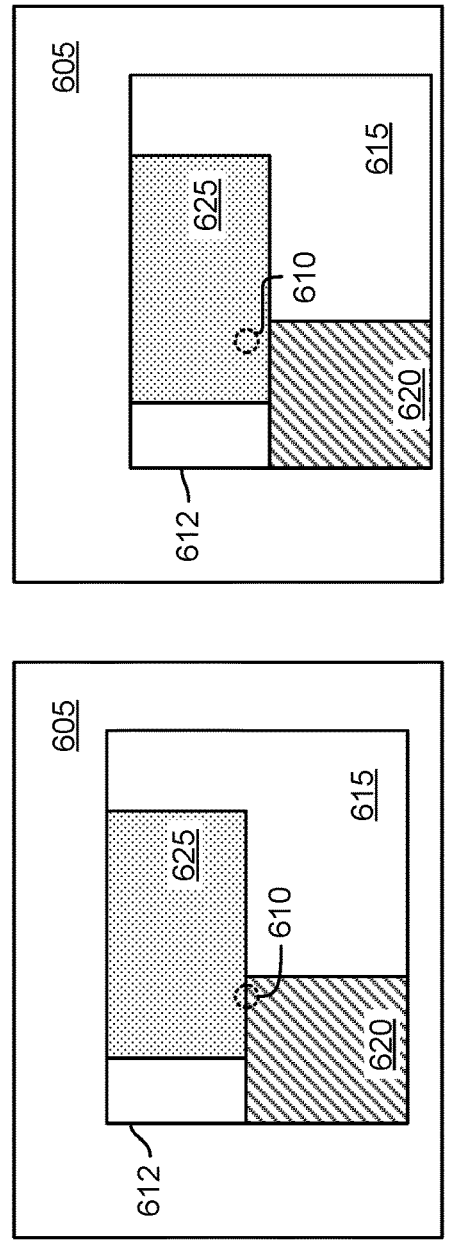

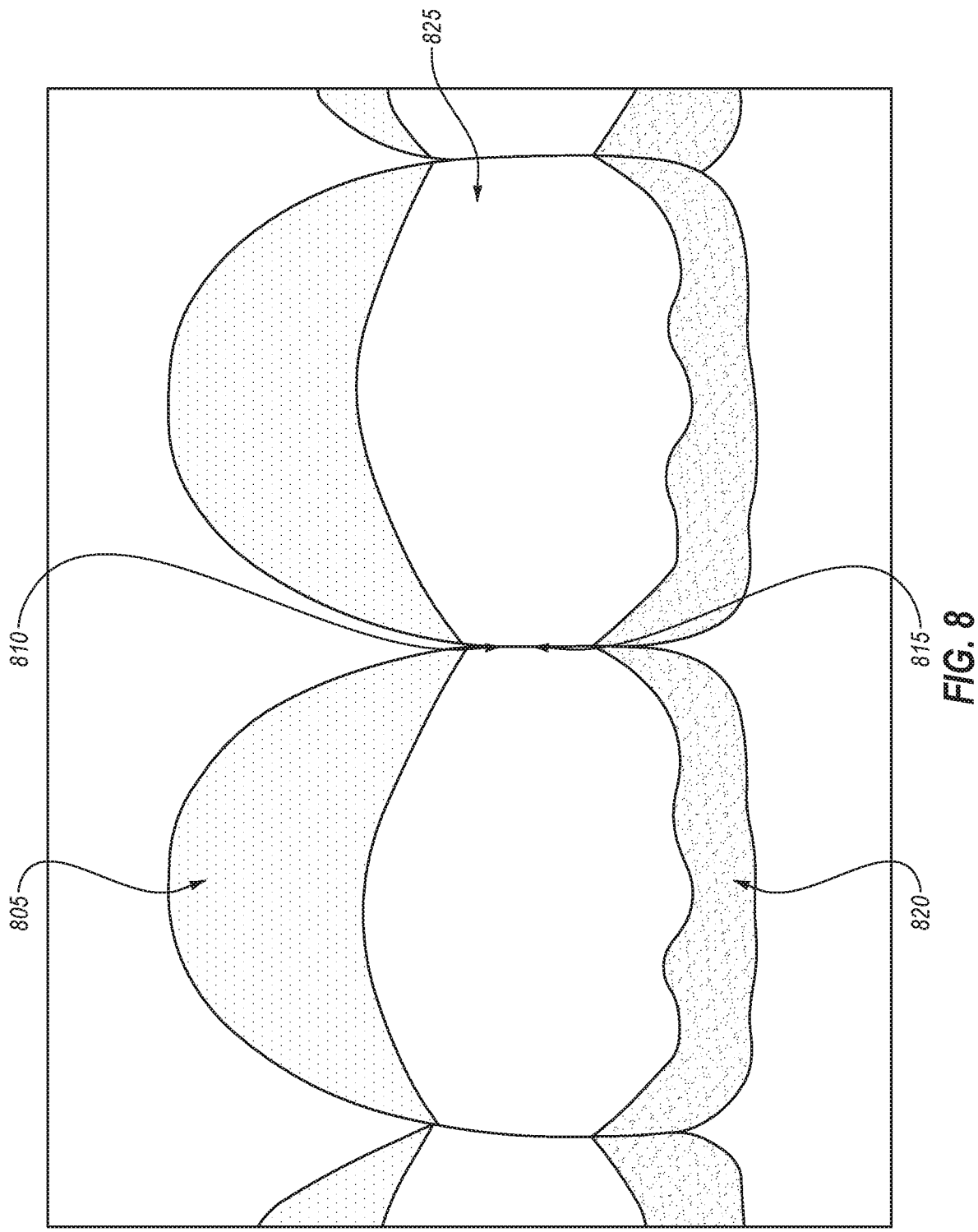

US 11,792,384 B2

PROCESSING COLOR INFORMATION FOR INTRAORAL SCANS

RELATED APPLICATIONS

This patent application is a continuation of U.S. patent application Ser. No. 15/953,268, filed Apr. 13, 2018, which claims the benefit under 35 U.S.C. § 119(e) of U.S. Provisional Application No. 62/520,417, filed Jun. 15, 2017, both of which are incorporated by reference herein.

TECHNICAL FIELD

Embodiments of the present invention relate to the field of imaging and, in particular, to a system and method for performing imaging of a three dimensional surface and for accurately determining colors of locations on the three dimensional surface.

BACKGROUND

Intraoral scanners have been developed for direct optical measurement of teeth and the subsequent automatic manufacture of dental appliances such as aligners, bridges, crowns, and so on. The term "direct optical measurement" signifies surveying of teeth in the oral cavity of a patient. Intraoral scanners typically include an optical probe coupled to an optical scanning system, which may include optics as well as an optical pick-up or receiver such as charge coupled device (CCD) or complementary metal-oxide semiconductor (CMOS) sensor. The optical scanning systems of intraoral scanners are generally able to generate three dimensional images with accurate shape. However, the optical scanning systems of Intraoral scanners generally have inaccurate color sensing capabilities.

Due to the inability of intraoral scanners to accurately generate color data for a patient's teeth, tooth coloring for dental prosthetics such as crowns and bridges are primarily performed manually by eye. However, the current practice of manually coloring dental prosthetics by eye is time consuming and inefficient.

BRIEF DESCRIPTION OF THE DRAWINGS

The present invention is illustrated by way of example, and not by way of limitation, in the figures of the accompanying drawings.

FIG. 2C illustrates optics of a color sensor for an imaging apparatus, in accordance with another embodiment.

FIGS. 6A-E are figures showing calibration of a color sensor to a detector of an imaging apparatus.

FIG. 8 is a diagram of tooth color zones.

DETAILED DESCRIPTION

Figure 1A:
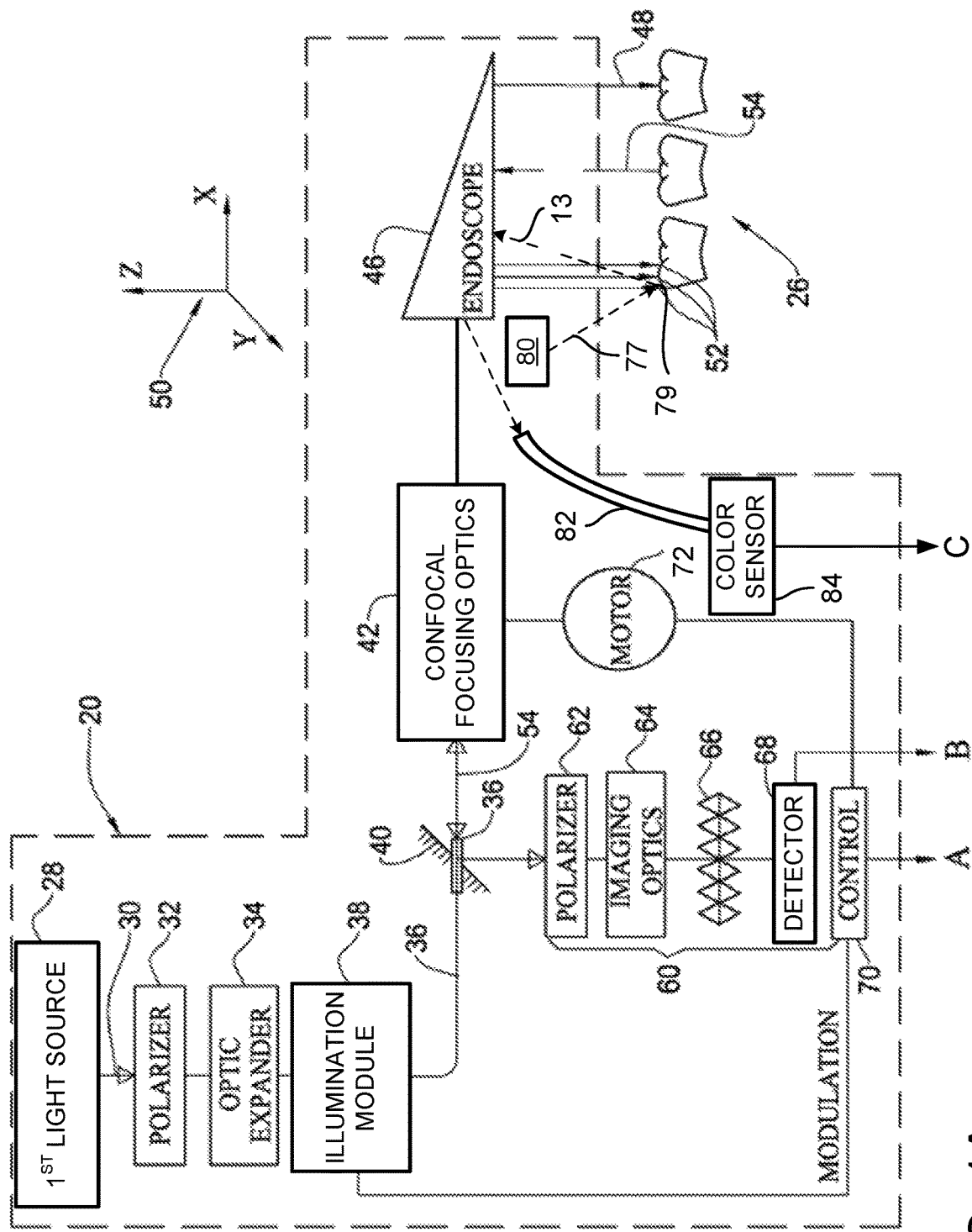
FIG. 1A illustrates a functional block diagram of an imaging apparatus according to one embodiment.

Described herein is an imaging apparatus that includes both an optical scanning system capable of generating three dimensional images of three dimensional objects and a color sensor capable of taking highly accurate color measurements of locations (e.g., spots) on the three dimensional objects. For many dental procedures it is important to know both the three dimensional shape of one or more teeth as well as to know the colors of the one or more teeth. For example, a tooth crown should be the same shape as an original tooth or neighboring teeth and should have the same shading as that original tooth. If the shape is incorrect, then the crown may not fit in a patient's mouth. If the color of any portion of the crown is incorrect, then the crown shading will not match the shading of the patient's other teeth and the crown will be highly noticeable to viewers. Accordingly, dental practitioners and dental technicians often need accurate color data of multiple different portions of a patient's tooth in addition to accurate three dimensional shape data of the tooth.

In one embodiment, an imaging apparatus includes a first light source (e.g., a laser and illumination module) to generate an array of light beams. The imaging apparatus additionally includes a probe and focusing optics along an optical path of the array of light beams to direct the array of light beams through the probe. The probe directs the array of light beams toward a three dimensional object to be imaged. The array of light beams reflect off of the three dimensional object, and an array of returning light beams are reflected back into the probe and through the focusing optics. A detector detects the array of returning light beams and generates measurements of the array of returning light beams. The measurements of the array of returning light beams indicate a shape of the three dimensional object.

The imaging apparatus additionally includes a second light source to generate multi-chromatic light that is to illuminate the three dimensional object. Rays of the multi-chromatic light is reflected off of the three dimensional object and into the probe. One or more of the rays are collected by an optical transmission medium that is outside of the optical path of the focusing optics in one embodiment. The one or more rays are rays that have been reflected off of a spot on the three dimensional object, where the spot is within the receptive view of a color sensor. The optical transmission medium guides the one or more rays to color sensor, which may be a spectrometer, colorimeter or hyper spectral sensor that is optically coupled to an end of the optical transmission medium. The spectrometer, colorimeter or hyper spectral sensor receives the one or more rays of the multi-chromatic light and determines a color of the spot on the three dimensional object based on an analysis of the one or more rays. The color information of the spot and the three dimensional shape information of the three dimensional object may be transmitted to a computing device connected to the imaging apparatus.

In an alternative embodiment, the optical transmission medium may be omitted. In such an embodiment, the color sensor may be placed near to, and outside of, the optical path of the focusing optics. The color sensor may be oriented at an oblique angle to the optical path. One or more rays of the multi-chromatic light that reflected off of the three dimensional object and into the probe will also have an oblique angle to the optical path of the focusing optics. These one or more rays will be collected by the color sensor. The one or more rays are rays that have been reflected off of a spot on the three dimensional object, where the spot is within the receptive view of the color sensor. It should be understood that any of the embodiments discussed herein with reference to inclusion of an optical transmission medium may also be implemented without the optical transmission medium.

The three dimensional shape information generated by the detector is very accurate, and is usable to construct a three dimensional model of the object that is imaged (e.g., of a tooth or entire jaw of a patient). The color data is for small spots on the imaged object, but is highly accurate. The color data can be combined with the three dimensional shape data by the computing device to generate a three dimensional model that includes both accurate shape information and accurate color information. The three dimensional model can facilitate manufacture of dental prosthetics that accurately reflect the shape and color of a tooth or teeth to be replaced by providing improved color description.

Embodiments are discussed herein with reference to a confocal imaging apparatus that includes an accurate color sensor. For example, embodiments discuss a confocal imaging apparatus with confocal focusing optics that direct an array of light beams through a probe onto a three dimensional object. The confocal imaging apparatus additionally includes an optical transmission medium that collects multi-chromatic light rays outside of an optical path of the confocal focusing optics and a color sensor outside of the optical path of the confocal focusing optics that receives the multi-chromatic light rays from the optical transmission medium. However, it should be understood that embodiments also apply to other types of three dimensional imaging apparatuses that include an accurate color sensor. Examples of other types of 3D imaging apparatuses include apparatuses that measure time of flight of laser light, apparatuses that use triangulation from multiple lasers and detectors at different positions and orientations relative to an imaged object, apparatuses that project structured light onto an object and measure how the structured light pattern changes to determine a 3D shape, apparatuses that use modulated light, apparatuses that use multiple detectors for stereoscopic imaging, apparatuses that include photometric systems that use a single detector to generate multiple images under varying light conditions to determine a 3D shape, and so on. The embodiments discussed herein with reference to a confocal imaging apparatus may apply equally well to any of the other types of 3D imagers, such as those provided above. In such alternative embodiments, an optical transmission medium and color sensor (e.g., colorimeter, spectrometer or hyper spectral sensor) may be positioned outside of the optical path of the detectors and/or 3D scanning optics that are used to generate 3D images of an object. The optical transmission medium collects multi-chromatic light that is outside of the optical path of the 3D scanning optics, and directs the multi-chromatic light to the color sensor, as is described in embodiments herein below.

Figure 1B:
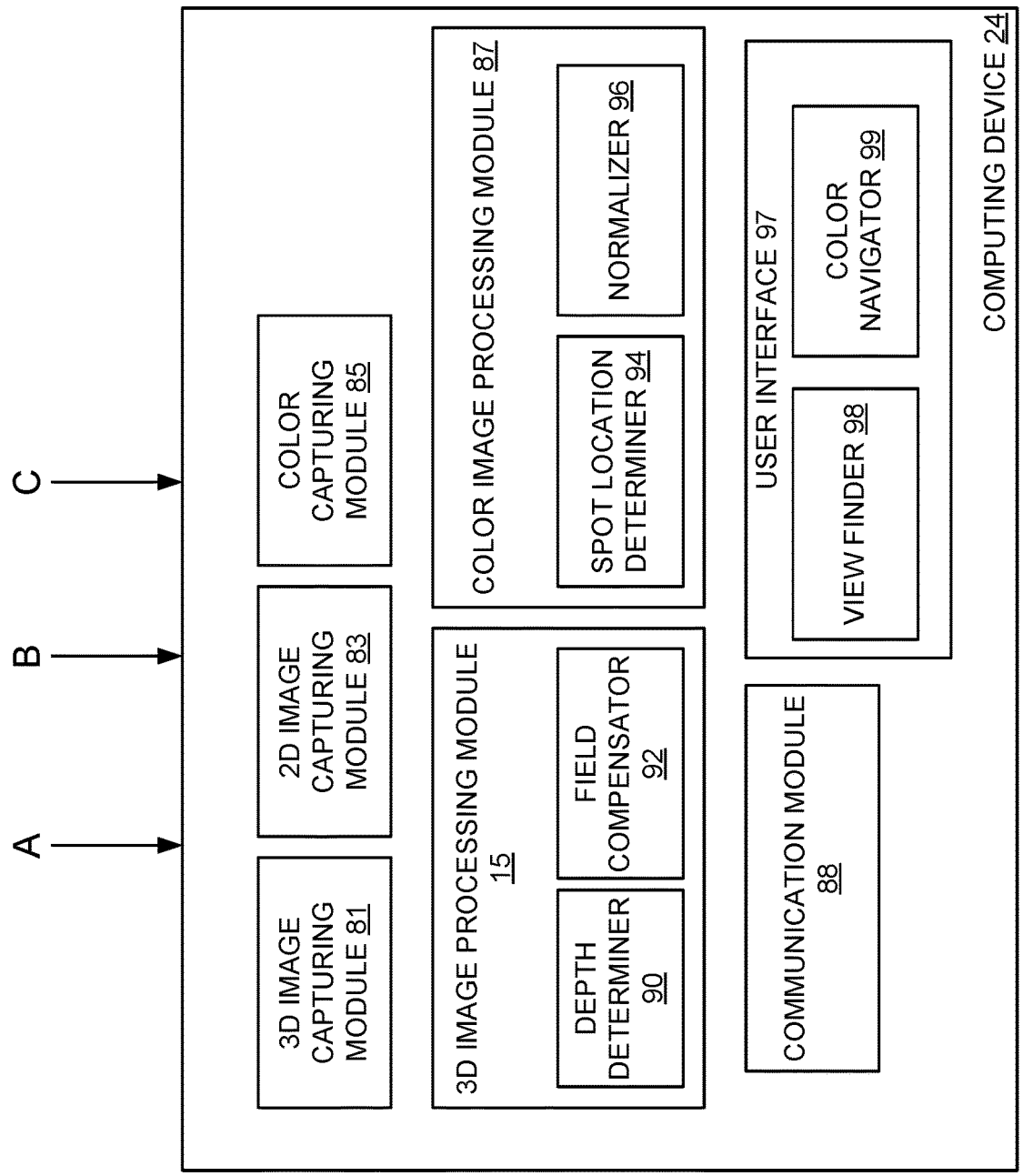
FIG. 1B illustrates a block diagram of a computing device that connects to an imaging apparatus, in accordance with one embodiment.

FIG. 1A illustrates a functional block diagram of an imaging apparatus 20 according to one embodiment. In one embodiment, the imaging apparatus 20 is a confocal imaging apparatus. FIG. 1B illustrates a block diagram of a computing device 24 that connects to the imaging apparatus 20. Together, the imaging apparatus 20 and computing device 24 may form a system for generating three dimensional images of scanned objects and for generating color data of spots on the scanned objects. The computing device 24 may be connected to the imaging apparatus 20 directly or indirectly and via a wired or wireless connection. For example, the imaging apparatus 20 may include a network interface controller (NIC) capable of communicating via Wi-Fi, via third generation (3G) or fourth generation (4G) telecommunications protocols (e.g., global system for mobile communications (GSM), long term evolution (LTE), Wi-Max, code division multiple access (CDMA), etc.), via Bluetooth, via Zigbee, or via other wireless protocols. Alternatively, or additionally, imaging apparatus 20 may include an Ethernet network interface controller (NIC), a universal serial bus (USB) port, or other wired port. The NIC or port may connect the imaging apparatus to the computing device via a local area network (LAN). Alternatively, the imaging apparatus 20 may connect to a wide area network (WAN) such as the Internet, and may connect to the computing device 24 via the WAN. In an alternative embodiment, imaging apparatus 20 is connected directly to the computing device (e.g., via a direct wired or wireless connection). In one embodiment, the computing device 24 is a component of the imaging apparatus 20.

Referring now to FIG. 1A, in one embodiment imaging apparatus 20 includes a first light source 28, which may be a semiconductor laser unit that emits a focused light beam 30, as represented by an arrow. The focused light beam 30 may be a focused light beam of coherent light (e.g., laser light having a wavelength of 680 nm in an embodiment). The light beam 30 passes through a polarizer 32, which polarizes the light beam 30. Alternatively, polarizer 32 may be omitted in some embodiments. The light beam 30 may then enter into an optic expander 34 that improves a numerical aperture of the light beam 30. The light beam 30 may then pass through an illumination module 38 such as a beam splitter, which splits the light beam 30 into an array of light beams 36, represented here, for ease of illustration, by a single line. The illumination module 38 may be, for example, a grating or a micro lens array that splits, the light beam 30 into an array of light beams 36. In one embodiment, the array of light beams 36 is an array of telecentric light beams. Alternatively, the array of light beams may not be telecentric.

The imaging apparatus 20 further includes a unidirectional mirror or beam splitter (e.g., a polarizing beam splitter) 40 that passes the array of light beams 36. A unidirectional mirror 40 allows transfer of light from the semiconductor laser 28 through to downstream optics, but reflects light travelling in the opposite direction. A polarizing beam splitter allows transfer of light beams having a particular polarization and reflects light beams having a different (e.g., opposite) polarization. In one embodiment, the unidirectional mirror or beam splitter 40 has a small central aperture. The small central aperture may improve a measurement accuracy of the imaging apparatus 20. In one embodiment, as a result of a structure of the unidirectional mirror or beam splitter 40, the array of light beams will yield a light annulus on an illuminated area of an imaged object as long as the area is not in focus. Moreover, the annulus will become a completely illuminated spot once in focus. This ensures that a difference between measured intensities of out-of-focus points and in focus points will be larger.

In one embodiment, along an optical path of the array of light beams after the unidirectional mirror or beam splitter 40 are confocal focusing optics 42, and a probe 46 (e.g., such as an endoscope or folding prism). Additionally, a quarter wave plate may be disposed along the optical path after the unidirectional mirror or beam splitter 40 to introduce a certain polarization to the array of light beams. In some embodiments this may ensure that reflected light beams will not be passed through the unidirectional mirror or beam splitter 40. Confocal focusing optics 42 may additionally include relay optics (not shown). Confocal focusing optics 42 may or may not maintain the same magnification of an image over a wide range of distances in the Z direction, wherein the Z direction is a direction of beam propagation (e.g., the Z direction corresponds to an imaging axis that is aligned with an optical path of the array of light beams 36). The relay optics enable the imaging apparatus 20 to maintain a certain numerical aperture for propagation of the array of light beams 36.

The probe 46 may include a rigid, light-transmitting medium, which may be a hollow object defining within it a light transmission path or an object made of a light transmitting material, e.g. a glass body or tube. In one embodiment, the probe 46 includes a prism such as a folding prism. At its end, the probe 46 may include a mirror of the kind ensuring a total internal reflection. Thus, the mirror may direct the array of light beams towards a tooth 26 or other object. The probe 46 thus emits array of light beams 48, which impinge on to surfaces of the tooth 26.

The array of light beams 48 are arranged in an X-Y plane, in the Cartesian frame 50, propagating along the Z axis. As the surface on which the incident light beams hits is an uneven surface, illuminated spots 52 are displaced from one another along the Z axis, at different $(X_i, Y_i)$ locations. Thus, while a spot at one location may be in focus of the confocal focusing optics 42, spots at other locations may be out-of-focus. Therefore, the light intensity of returned light beams of the focused spots will be at its peak, while the light intensity at other spots will be off peak. Thus, for each illuminated spot, multiple measurements of light Intensity are made at different positions along the Z-axis. For each of such $(X_i, Y_i)$ location, the derivative of the intensity over distance (Z) may be made, with the $Z_i$ yielding maximum derivative, $Z_0$, being the in-focus distance. As pointed out above, the incident light from the array of light beams 48 forms a light disk on the surface when out of focus and a complete light spot when in focus. Thus, the distance derivative will be larger when approaching in-focus position, increasing accuracy of the measurement.

The light scattered from each of the light spots includes a beam travelling initially in the Z axis along the opposite direction of the optical path traveled by the array of light beams 48. Each returned light beam in an array of returning light beams 54 corresponds to one of the incident light beams in array of light beams 36. Given the asymmetrical properties of unidirectional mirror or beam splitter 40, the returned light beams are reflected in the direction of detection optics 60.

The detection optics 60 may include a polarizer 62 that has a plane of preferred polarization oriented normal to the plane polarization of polarizer 32. Alternatively, polarizer 32 and polarizer 62 may be omitted in some embodiments. The array of returning light beams 54 may pass through imaging optics 64 in one embodiment. The imaging optics 64 may be one or more lenses. Alternatively, the detection optics 60 may not include imaging optics 64. In one embodiment, the array of returning light beams 54 further passes through a matrix 66, which may be an array of pinholes. Alternatively, no matrix 66 is used in some embodiments. The array of returning light beams 54 are then directed onto a detector 68.

The detector 68 is an image sensor having a matrix of sensing elements each representing a pixel of the image. If matrix 66 is used, then each pixel further corresponds to one pinhole of matrix 66. In one embodiment, the detector is a charge coupled device (CCD) sensor. In one embodiment, the detector is a complementary metal-oxide semiconductor (CMOS) type image sensor. Other types of image sensors may also be used for detector 68. The detector 68 detects light intensity at each pixel.

In one embodiment, detector 68 provides data to computing device 24. Thus, each light intensity measured in each of the sensing elements of the detector 68, is then captured and analyzed, in a manner to be described below, by processor 24.

Confocal imaging apparatus 20 further includes a control module 70 connected both to first light source 28 and a motor 72, voice coil or other translation mechanism. In one embodiment, control module 70 is or includes a field programmable gate array (FPGA) configured to perform control operations. Motor 72 is linked to confocal focusing optics 42 for changing a focusing setting of confocal focusing optics 42. This may adjust the relative location of an imaginary flat or non-flat focal surface of confocal focusing optics 42 along the Z-axis (e.g., in the imaging axis). Control module 70 may induce motor 72 to axially displace (change a location of) one or more lenses of the confocal focusing optics 42 to change the focal depth of the imaginary flat or non-flat focal surface. In one embodiment, motor 72 or imaging apparatus 20 includes an encoder (not shown) that accurately measures a position of one or more lenses of the confocal focusing optics 42. The encoder may include a sensor paired to a scale that encodes a linear position. The encoder may output a linear position of the one or more lenses of the confocal focusing optics 42. The encoder may be an optical encoder, a magnetic encoder, an inductive encoder, a capacitive encoder, an eddy current encoder, and so on. After receipt of feedback that the location of the one or more lenses has changed, control module 70 may induce first light source 28 to generate a light pulse. Control unit 70 may additionally synchronize three dimensional (3D) image-capturing module 80 from FIG. 1B to receive and/or store data representative of the light intensity from each of the sensing elements at the particular location of the one or more lenses (and thus of the focal depth of the imaginary flat or non-flat focal surface). In subsequent sequences, the location of the one or more lenses (and thus the focal depth) will change in the same manner and the data capturing will continue over a wide focal range of confocal focusing optics 42. Since the first light source 28 is a coherent light source, the 3D image data generated by detector 68 based on the light beam 30 is a monochrome image.

Confocal imaging apparatus 20 additionally includes one or more second light source 80. In some embodiments the second light source 80 is actually multiple light sources arranged at various positions on the probe 46. The multiple different light sources may provide the same type of light, but may each provide the light from different directions and/or positions. The second light source 80 may be a multi-chromatic light source such as a white light source. The second light source 80 may be, for example, one or more incandescent light, one or more light emitting diodes (LEDs), one or more halogen lights, or other types of light sources. In one embodiment, the second light source 80 emits visible light at wavelengths of about 400-650 nm. The second light source 80 may be positioned internally or externally to the endoscope to shine light directly on the tooth 26. In such an embodiment, the second light source 80 may not shine light through the probe 46 onto the teeth. In an alternative embodiment, the second light source 80 may be internal to the imaging apparatus 20, and may shine light along the optical path of the confocal focusing optics 42 and/or into the probe 46. The probe 46 may then emit the multi-chromatic light to illuminate the tooth 26.

The multi-chromatic light is reflected off of the tooth 26, and a plurality of reflected rays of the multi-chromatic light enter the probe 46 and travel through the confocal focusing optics 42 and into the detection optics 60. The multi-chromatic light received by the detection optics 60 may not be focused light (e.g., may not be laser light), and may not be used to detect a 3D shape of the tooth 26. Instead, the multi-chromatic light may enter the sensing elements of the detector 68 to generate a 2D image of the tooth.

Detecting optics 60 may include a set of color filters, which may include a red color filter, a blue color filter and a green color filter. In one embodiment, detecting optics 60 include a Bayer-pattern color filter. The Bayer-pattern color filter may include a set of 4-pixel RGGB (red, green, green, blue) groups, where each RGGB group determines a color for four adjacent pixels. The color filters filter out the multi-chromatic light rays impinging on particular sensors of the detector 68, and are usable to generate a color 2D image of the tooth. These color filters may be low accuracy pigment based absorption color filters. Each of the color filters may have a relatively wide bandwidth. The spectral overlap between the color filters and the use of only three basic colors results in an inaccurate color separation ability. As a result, the green color filter may pass some blues and greens, the blue color filter may pass some greens and reds, and so on. Accordingly, the color 2D image of the tooth has a low color accuracy.

In addition to generating image data (e.g., a collection of 2D images with varying focus settings) usable to generate a highly accurate 3D monochrome image of the tooth 26, detection optics 60 and/or detector 68 may be usable to generate a 2D color image of the tooth 26. The 2D color image data may be sent to a 2D image capturing module 83 of computing device 24 of FIG. 1B. Confocal imaging apparatus 20 may alternate between use of the first light source 28 to generate first image data for a 3D image of the tooth 26 and second light source 80 to generate second image data for a color 2D image of the tooth 26. Confocal imaging apparatus 20 may rapidly alternate between use of the first and second light sources 28, 80. A scan rate of the detector 68 for the 3D image data and for the color 2D image data may be about 20 scans per second. The color 2D image data may be used to present a view finder image to a user during use of the imaging apparatus 20. This may facilitate accurate placement of the imaging apparatus 20 in a patient's mouth and scanning of desired dental regions.

The color accuracy of the detector 68 is insufficient for some applications, such as estimating the shade (e.g., coloring) of prosthetic teeth. Accordingly, imaging apparatus 20 includes a very accurate color sensor 84 that determines a color of spots in a small receptive field (also referred to as a field of view (FOV)) of the color sensor 84. The receptive field is the region in space that the color sensor is sensitive to. The level of sensitivity is not uniform in the receptive field, and may have an approximately circular shape with smooth edges. As shown, one or more rays of multi-chromatic light 77 may reflect off of a small spot 79 on tooth 26 at an angle that is oblique to the imaging axis (e.g., that is oblique to the z axis in Cartesian frame 50). One or more rays 13 of multi-chromatic light may reflect off of the tooth 26 and enter probe 46 at an oblique angle to the imaging axis, and then exit the probe 46 at an oblique angle to the imaging axis. These one or more reflected rays 13 of multi-chromatic light then enter an optical transmission medium 82 that is oriented to receive the one or more rays 13 at a specific oblique angle to the imaging axis of the optical path for the confocal focusing optics 42. The oblique angle may be an angle of 2-60 degrees in one embodiment. In one embodiment, the oblique angle is an angle of 5-45 degrees. In one embodiment, the oblique angle is an angle of 5-30 degrees. Some exemplary angle ranges for the oblique angle include 5-10 degrees, 10-15 degrees, 15-20 degrees, 20-25 degrees and 25-30 degrees. Smaller angles may result in improved accuracy for determination of the location of the receptive field for the color sensor. Accordingly, in one embodiment, the oblique angle is 5-15 degrees. The optical transmission medium 82 is positioned outside of the optical path of the confocal focusing optics 42 so as not to occlude any returning light beams during 3D imaging. The optical transmission medium 82 may be a light pipe, optical fiber, light guide, and so on. In some embodiments, the optical transmission medium 82 is a flexible or semi-flexible optical fiber. Alternatively, the optical transmission medium 82 may be rigid. The optical transmission medium 82 may be, for example, an optical fiber that includes a transparent core surrounded by a transparent cladding material with a low index of refraction. The optical fiber may be made from silica, fluoride glass, phosphate glass, fluorozirconate, fluoroaluminate, chalcogenide glass, sapphire, plastic, or other materials. Plastic or polymer optical fibers may have a fiber core formed from Poly(methyl methacrylate) (PMMA) or Polystyrene, and may have a fiber cladding of, for example, silicone resin. Silica (glass) based optical fibers have less internal scattering and absorption than plastic based optical fibers. However, glass based optical fibers have a limited bending radius, while plastic based optical fibers have a larger bending radius.

In an alternative embodiment, the multi-chromatic light rays may reflect off of the spot 79 at an angle that is parallel to the imaging axis. In such an embodiment, a beam splitter (not shown) may be positioned between the probe 46 and the confocal focusing optics 42 along the optical path of the confocal imaging optics 42. The beam splitter may reflect some portion of the multi-chromatic light rays into the optical transmission medium 82.

The optical transmission medium 82 may direct the one or more rays 13 into the color sensor 84. The color sensor 84 may be a colorimeter, spectrometer or hyper spectral sensor (also referred to as a multi-spectral sensor). A spectrometer is a special case of a hyper spectral sensor. The hyper spectral sensor (or spectrometer) is able to determine the spectral content of light with a high degree of accuracy. The color sensor 82 is able to determine with a high degree of accuracy a color spectrum of the small spot 79 by determining, for example, intensities of the light as reflected off of the spot 79 at many different light wavelengths. The relative intensities of the different wavelengths provide a highly accurate color measurement of the spot 79. The wavelength separation achievable by the hyper spectral sensor can be as good as a few nanometers or tens of nanometers. Additionally, in hyper spectral sensors the use of interference filters allows for an overlap between various colors. Color sensor 84 may alternatively be a colorimeter.

A colorimeter is a device that mimics the human color response, and can be used for exact color definition. Color sensor 84 may additionally send the color measurement to a color capturing module 85 of the computing device 24 of FIG. 1B.

In an alternative embodiment, the optical transmission 82 medium may be omitted. In such an embodiment, the color sensor 84 may be placed near to, and outside of, the optical path of the confocal imaging optics 42. The color sensor 84 may be oriented at an oblique angle to the optical path. One or more rays of the multi-chromatic light that are reflected off of the tooth 26 and into the probe 46 will also have an oblique angle to the optical path of the confocal imaging optics 42. The oblique angle may be an angle of 2-60 degrees in one embodiment. In one embodiment, the oblique angle is an angle of 5-45 degrees. In one embodiment, the oblique angle is an angle of 5-30 degrees. Some exemplary angle ranges for the oblique angle include 5-10 degrees, 10-15 degrees, 15-20 degrees, 20-25 degrees and 25-30 degrees. Smaller angles may result in improved accuracy for determination of the location of the receptive field for the color sensor. Accordingly, in one embodiment, the oblique angle is 5-15 degrees. These one or more rays will be collected by the color sensor 84. The one or more rays are rays that have been reflected off of a spot on the tooth 26, where the spot is within the receptive view of a color sensor 84.

In some embodiments the second light source 80 emits light at approximately 405 nm. Alternatively, a third light source may be included that emits the light at approximately 405 nm. Light at this wavelength causes the tooth 26 to fluoresce when the light impacts the tooth 26. The color sensor 84 may measure the magnitude of fluorescence of the tooth 26 at the spot 79. The level of tooth fluorescence may indicate a health of the tooth 26. In one embodiment, a filter which rejects the light source 80 from reaching the color sensor 84 may be included. The filter can prevent oversaturation of the hyper spectral sensor.

In one embodiment, the first light source 28 and second light source 80 are used one at a time. For example, first light source 28 is activated and detector 68 generates one or more images, then first light source 28 is deactivated and second light source 80 is activated and detector 68 generates one or more additional images. While the second light source 80 is active, color sensor 84 additionally generates a color measurement. The second light source 80 is then deactivated and the first light source 28 is reactivated and the detector 68 generates one or more additional images, and so on.

In one embodiment, detector 68 is not used to generate 2D images. In such an embodiment, color sensor 84 may generate color measurements at the same time as detector 68 generates 3D image data. For example, a filter (not shown) may be disposed between probe 46 and confocal focusing optics 42. The filter may filter out the multi-chromatic light from the second light source 80 and may pass the light from the first light source 28. Accordingly, the first light source 28 and second light source 80 may be activated in parallel, and color measurements and 3D measurements may be taken in parallel.

Referring now to FIG. 1B, 3D image capturing module 81 may capture images for 3D imaging responsive to receiving first image capture commands from the control unit 70. The captured images may be associated with a particular focusing setting (e.g., a particular location of one or more lenses in the confocal focusing optics as output by the encoder). 3D Image processing module 82 then processes captured images captured over multiple different focusing settings. 3D image processing module 15 includes a depth determiner 90 and may include a field compensator 92 for processing image data.

Depth determiner 90 determines the relative intensity in each pixel over the entire range of focal settings of confocal focusing optics 42 from received image data. Once a certain light spot associated with a particular pixel is in focus, the measured intensity will be maximal for that pixel. Thus, by determining the $Z_i$ corresponding to the maximal light intensity or by determining the maximum displacement derivative of the light intensity, for each pixel, the relative position of each light spot along the Z axis can be determined for each pixel. Thus, data representative of the three-dimensional pattern of a surface in the teeth segment 26 or other three dimensional object can be obtained.

In some embodiments where the imaging apparatus has a curved field, field compensator 92 may compensate for the curved field caused by the lack of a field lens 2D image capturing module 83 may receive color 2D image data from the imaging apparatus 20. The color 2D image data may then be used to output a real time image of a FOV of the imaging apparatus 20. The real time image may be output to a view finder 98 via a user interface 97 of the computing device 24. A user may view the view finder in a display to determine how the imaging apparatus is positioned in a patient's mouth.

As mentioned, the imaging apparatus 20 may alternate between use of detector 68 to generate 3D monochrome image data and use of detector 68 to generate color 2D image data. Accordingly, the computing device 24 may alternately receive image data usable by 3D image capturing module 82 and 3D image processing module 15 to generate a 3D image of an object and receive image data usable by 2D image capturing module 83 to generate a color 2D image of the object.

As 3D images are generated by 3D image processing module 15, 3D image processing module 15 may stitch those 3D images together to form a virtual 3D model of an imaged object (e.g., of a patient's tooth and/or dental arch). The user interface 97 may be a graphical user interface that includes controls for manipulating the virtual 3D model (e.g., viewing from different angles, zooming-in or out, etc.). In addition, data representative of the surface topology of the scanned object may be transmitted to remote devices by a communication module 88 for further processing or use.

By capturing, in this manner, an image from two or more angular locations around the structure, e.g. in the case of a teeth segment from the buccal direction, from the lingual direction and optionally from an occlusal portion of the teeth, an accurate three-dimensional representation of a tooth may be reconstructed. This may allow a virtual reconstruction of the three-dimensional structure in a computerized environment or a physical reconstruction in a CAD/CAM apparatus. For example, a particular application is imaging of a segment of teeth having at least one missing tooth or a portion of a tooth. In such an instance, the image can then be used for the design and subsequent manufacture of a crown or any other prosthesis to be fitted onto a dental arch of a patient.

Color capturing module 85 receives color measurements of spots on an imaged object. The color measurements may be generated in parallel to 2D color images in embodiments. The computing device may alternately receive color data and 3D imaging data in some embodiments. In other embodiments, the color measurements may be generated in parallel to 3D monochrome images.

Color image processing module 87 processes color measurement data to determine a location on an object that has a particular color and to determine what that particular color is. In one embodiment, color image processing module 87 includes a spot location determiner 94 and a normalizer 96.

When color capturing module 85 receives color measurement data, spot location determiner 94 is responsible for determining a location on an imaged object to associate with the color measurement data. In one embodiment, the color sensor 84 has a small receptive field at a known position within a larger FOV of the confocal focusing optics 42 and detector 68. The receptive field is small relative to the object that is being scanned and/or to the size of a constant color region of the object being scanned. Color capturing module 85 may receive a color measurement commensurate with 2D image capturing module 83 receiving a color 2D image. The position of the receptive field of the color sensor in the larger FOV may be used to determine a spot on the color 2D image that has the color of the received color measurement in an embodiment. Alternatively, color capturing module 85 may receive a color measurement commensurate with 3D image capturing module 81 receiving a 3D image. The position of the receptive field of the color sensor in the larger FOV may be used to determine a spot on the 3D image that has the color of the received color measurement in an embodiment. The color measurement data may be synchronized with the 3D image data or the 2D image data so that they are generated at a constant interval from one another. Alternatively the color measurement data may be unsynchronized with the 3D or 2D data. In such a case, any of the data types may include a timestamp which indicates when they were taken. The timestamp may be used to decide the timing relation between them.

In another embodiment, a 3D location of a spot to associate with the color measurement data may be determined using multiple 3D images. A first 3D image may be generated shortly before a color measurement is made, and a second 3D image may be generated shortly after the color measurement is made. A location of the receptive field of the color sensor within the larger FOV of the detector may be determined for the first 3D image and the second 3D image, though no color measurements were taken at the times that these two images were generated. A location of a spot on an object for which the color measurement was taken may then be determined by interpolating between the location of the receptive field of the color sensor in the first 3D image and the location of the receptive field of the color sensor in the second 3D image. For example, an average of the locations of the receptive field of the color sensor in the first and second 3D images may be computed. The 3D images and the color measurements may each be generated at a scan rate of up to 20 measurements/images per second. Accordingly, the imaging apparatus will have moved at most only a small distance between taking of the first and second 3D images. As a result, the interpolated position of the spot measured by the color sensor is highly accurate in embodiments.

An intensity of the color measurement received by color capturing module 85 may vary depending on variables such as angle of incidence and distance of the probe 46 from a measured object. In particular, characteristics of light impacting an object include a) the light source spectrum and angles, b) angle of incidence from the light source to the object and c) strength or intensity of light impacting the object, which depends on a distance between the object and the light source. Additionally, the color measurement may also be based on object color and reflectance properties, such as what is absorbed (e.g., what wavelengths of light are absorbed and at what levels) at particular angles, what is reflected (e.g., what wavelengths of light are reflected and at what levels) at particular angles and what is diffused (e.g., what wavelengths of light are absorbed and at what levels) at particular angles. These values may vary depending on angle and wavelength. Additionally, characteristics of the image capturing may also affect the color measurement, such as angles of the rays that would be collected and the distance of the object from the collecting device.

Accordingly, normalizer 96 is responsible for normalizing color measurement data so that the final measurement does not depend on such variables as those outlined above. Once the spot location determiner 94 determines a location of a spot on the 3D object that has been measured for color, an angle of incidence of a ray of light that reflected off of that spot and was received by the color sensor may be determined. The 3D image provides a 3D surface of the spot. An angle of rays on the spot (e.g., in the receptive field) that are detected by the color sensor may be known with respect to an imaging axis. Accordingly, the known angle of the ray with respect to the imaging axis and the 3D surface of the object may be used to compute an angle of incidence of the ray with the spot on the 3D object. The intensity of the color measurement data may then be adjusted based on the determined angle of incidence. In one embodiment, a normalization table is used to adjust the intensity, where the normalization table indicates a multiplier to multiply by the intensity values of the color measurement based on the angle of incidence. Additionally, the other parameters set forth above may be known or computed, and these known or computed parameters may be used to further normalize the intensity values for the various wavelengths.

Note that calibration and normalization techniques are described herein with regards to calibrating and normalizing for color measurements of a color sensor such as a hyper spectral sensor, spectrometer or colorimeter. However, in embodiments the calibration and normalization techniques described herein may also be used to calibrate and normalize the detector for generating a 2D color image. For example, a spectral reflection of a region of the target may be measured by the detector at a known distance of the target from the scanner. The color sensitivity of the detector may then be calibrated and normalized as described herein with reference to calibration and normalization of the hyper spectral sensor. For example, the color sensitivity of the detector may be calibrated and normalized based at least in part on the first spectral reflection as measured by the detector, an angle of incidence from a light source to the first region of the target and the first distance. Other parameters that may also be used for the calibration and normalization include a) light source spectrum and angles, b) angle of incidence from the light source to the object and c) strength or intensity of light impacting the object, which depends on a distance between the object and the light source. Additionally, the color measurement may also be based on object color and reflectance properties, such as what is absorbed (e.g., what wavelengths of light are absorbed and at what levels) at particular angles, what is reflected (e.g., what wavelengths of light are reflected and at what levels) at particular angles and what is diffused (e.g., what wavelengths of light are absorbed and at what levels) at particular angles. These values may vary depending on angle and wavelength. Additionally, characteristics of the image capturing may also affect the color measurement, such as angles of the rays that would be collected and the distance of the object from the collecting device. All of these parameters may be known or computed, and these known or computed parameters may be used to calibrate and normalize the intensity values for the various wavelengths measured by the detector.

Intensity may also be affected by distance of the probe from the imaged object. A field of view depth of the confocal focusing optics is known, and the distance can be determined based on the 3D images and determined position of the spot in the 3D images. Once the distance is determined, another multiplier may be applied to the intensity based on the determined distance. The distance multiplier may be determined from a table that relates distances to multiplier values, for example.

Normalizer 96 may additionally apply other normalization factors in addition to the normalization factors for distance and angle of incidence. For example, normalizer 96 may automatically subtract known color sensor offsets of the color sensor from the color measurement. The color sensor offsets may have been determined during calibration of the imaging apparatus. After normalization, the detected color should be a true color, and two different imaging devices should measure approximately the same color regardless of distance and/or angle of incidence. Normalizer 96 may also take into account a specific spectrum of the multi-chromatic light source (e.g., a specific white illumination source). Normalizer 96 may calibrate both for specific wavelength responses of the color sensor as well as the light source spectrum.

Color capture of spots on an imaged object may be performed in two modes of operation. In a first mode of operation, colors of spots on an imaged object are determined during 3D scanning of the object. In such an embodiment, color spectrum measurements may be automatically generated while 3D scanning is performed. The detector and the color sensor of the image capture device may have a high scanning rate (e.g., of 10-30 images per second). Accordingly, color measurements of many spots of an object (e.g., of a tooth) may be generated during 3D scanning.

In a second mode of operation, color navigator 99 provides a graphical interface that identifies color zones of a tooth and indicates which color zones still need one or more color measurements. A tooth is divided into multiple color zones, where each color zone indicates a separate region of the tooth that should have a relatively uniform color. However, color of the tooth may vary between color zones. FIG. 8 is a diagram of tooth color zones. As shown, a tooth may be divided into a cervical zone 805, interproximal zones 810, 815 on either side of the tooth, a body zone 825 and an incisal zone 820. In order to generate a prosthetic tooth that will blend in with other teeth in a patient's mouth, separate color measurements should be made of each of these color zones.

In some instances, the second mode of operation may be invoked after a 3D scan has been completed. For example, the 3D scan may lack color measurements for one or more color zone of a tooth. When the second mode is invoked, an image of a scanned tooth may be presented, with an overlay that indicates which color zones of the tooth have not yet been measured for color. If color measurements were generated during 3D scanning, then at least some of the color zones should be populated with color measurement information from one or multiple color measurements.

Returning to FIG. 1B, while in the second mode of operation, a user may move an imaging device (e.g., an intraoral scanner) to point the probe of the imaging device at a region of a tooth associated with a particular color zone for which color information is lacking. The user interface may display a cross hairs, circle, or other indicator or marker that identifies a location of a receptive field of the color sensor in the view finder 98, Accordingly, a user may move the imaging device until the cross hairs are pointed at a region of a tooth associated with a color zone that lacks color data or that has insufficient color data. The user interface 97 may provide a visual and/or audible signal when the probe is positioned for measurement of a region associated with such a color zone. The user may then initiate a color measurement (e.g., by pressing a button on the imaging device), and color capturing module 85 may receive the new color spectrum measurement. Color navigator 99 may then update the display to show that color information has been received for a particular tooth color zone (e.g., by coloring the tooth color zone green). In one embodiment, color navigator 99 updates the display once a threshold number of color measurements are generated for a color zone. The threshold may be, for example, 3, 5, or another number. Additionally, the image of the tooth may be updated using the received color information. This process may continue until color data is received for all tooth color zones. In some embodiments, the color image processing module 87 categorizes the colors of the different tooth color zones according to a color pallet, which may be a standard color pallet used for dental prosthetics. The color information may be recorded in an appropriate format along with the 3D shape information for use by a dental lab.

In some embodiments, color navigator 99 determines when an angle of incidence of light rays that reflect off of a spot on the object in the receptive field of the color sensor and are collected into the color sensor are too high or are within a spectral reflection angle. Color navigator 99 may additionally detect specular reflections. Color navigator 99 may provide feedback instructing a user to change the angle or orientation of the imaging apparatus to move outside of the spectral or specular reflection angles and/or to reduce the angle of incidence.

Figure 2A:
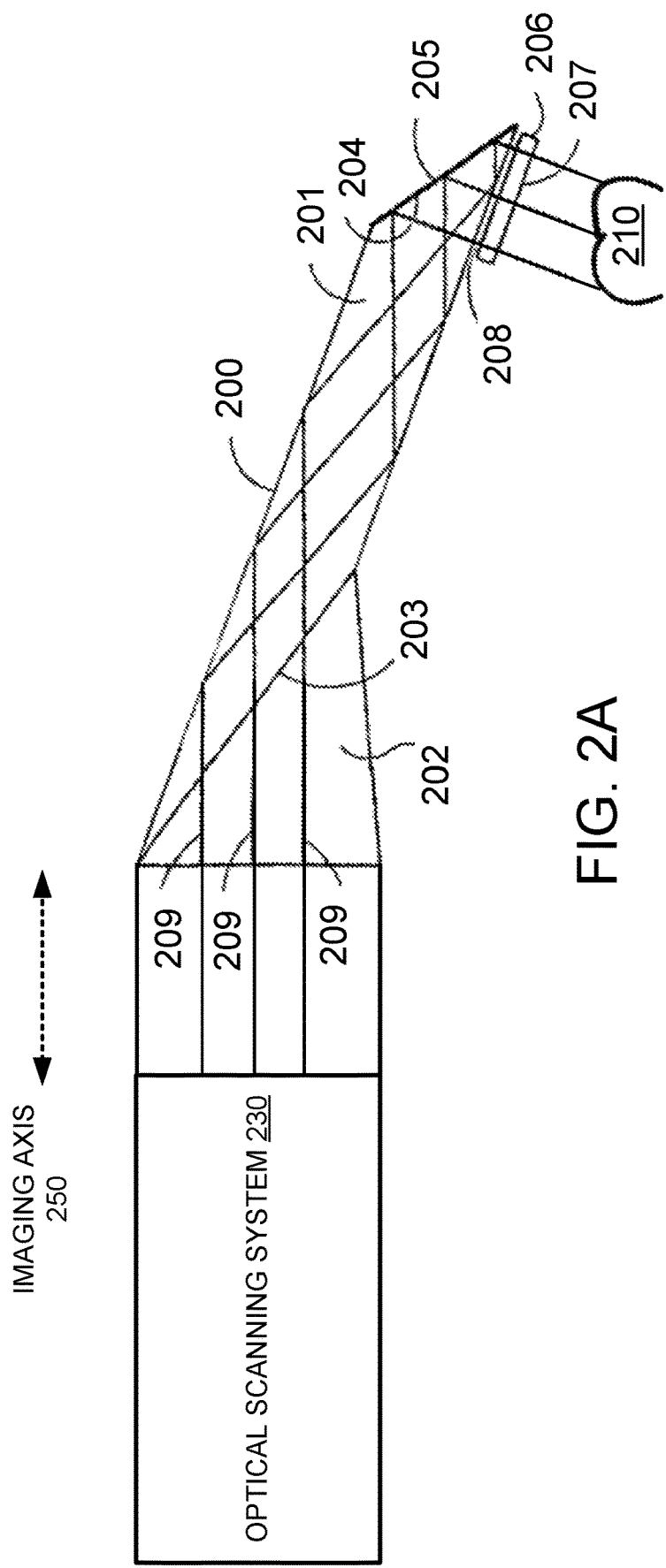
FIG. 2A illustrates optics of an optical scanning system of an imaging apparatus, in accordance with one embodiment.
Figure 2B:
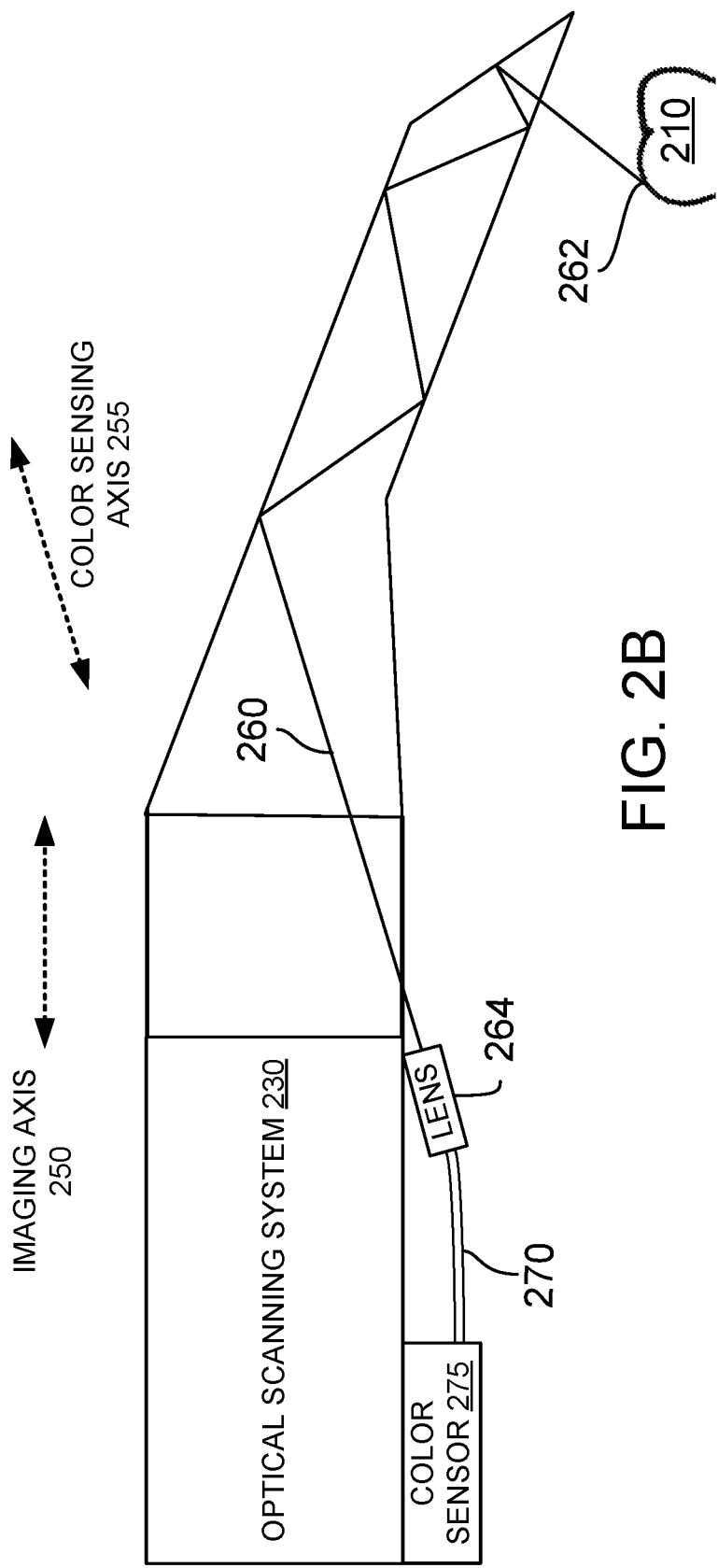
FIG. 2B illustrates optics of a color sensor for an imaging apparatus, in accordance with one embodiment.

FIG. 2A illustrates light rays entering an optical scanning system 230 of an imaging apparatus 197, in accordance with one embodiment. FIG. 2B illustrates light rays entering a color sensor 275 for the imaging apparatus 197 of FIG. 2A, in accordance with one embodiment. FIG. 2C illustrates light rays entering a color sensor 275 for an imaging apparatus 199, in accordance with another embodiment. Imaging apparatus 199 may be identical to imaging apparatus 197 in embodiments except for the addition of a beam splitter 276 and the positioning of an optical transmission medium 270 and lens 264.

Each of FIGS. 2A-B illustrate a probe 200 that directs light rays towards an optical scanning system 230 and/or toward a color sensor 275. The probe 200 is made of a light transmissive material such as glass. In one embodiment, the probe 200 acts as a prism (e.g., as a folding prism). Probe 200 may include an anterior segment 201 and a posterior segment 202, tightly bonded (e.g., glued) in an optically transmissive manner at 203. Probe 200 may additionally include a slanted face 204 covered by a reflective mirror layer 205. A window 206 defining a sensing surface 207 may be disposed at a bottom end of the anterior segment 201 in a manner leaving an air gap 208. The window 206 may be fixed in position by a holding structure which is not shown.

Referring to FIG. 2A, an array of light rays or beams 209 are represented schematically. As can be seen, the array of light beams 209 are reflected at the walls of the probe 200 at an angle in which the walls are totally reflective and finally reflect on mirror layer 205 out through the sensing face 207. The array of light beams 209 impact tooth 210, and the array of light beams 209 are directed back through the probe, along an imaging axis 250 of the optical scanning system 230 on an optical path for the optical scanning system 230, and into optical scanning system 230. The term optical scanning system 230 is used herein as a short hand to refer to the optics, additional components and detector (e.g., confocal focusing optics 12, detecting optics 60 and detector 68 of FIG. 1A) that are usable to generate a 3D image of the tooth 210. If the imaging apparatus 197 is a confocal imaging apparatus, then the optical scanning system 230 includes confocal focusing optics. However, the imaging apparatus 197 may use any 3D imaging techniques, and is not limited to a confocal imaging apparatus.

As shown, the array of light beams 209 remain within an optical path of the optical scanning system 230 so that all of the light beams in the array of light beams 209 enter the optical scanning system 230. For example, as shown all of the rays in the array of light beams 209 are parallel to the imaging axis 250.

The imaging apparatus 197 includes a color sensor 275 as described herein above. An optical transmission medium 270 optically connects the color sensor 275 to a lens 264 or other optical collector. The lens 264 is oriented so as to collect light beams or rays that exit the optical path of the optical scanning system 230 and that have a particular oblique angle to the imaging axis 250. As shown, none of the light beams in the array of light beams 209 enter lens 264, optical transmission medium 270 or color sensor 275 of the imaging apparatus 197.

Referring to FIG. 2B, one or more multi-chromatic light rays 260 are incident on a spot 262 on the tooth 210. The one or more multi-chromatic light rays 260 are reflected through window 206 into probe 200, and exit the probe 200 at an angle that is oblique to the imaging axis 250. The multi-chromatic light rays 260 exiting the probe 200 are parallel to a color sensing axis 255. The color sensing axis 255 has an oblique angle to the imaging axis 250. The lens 264, which may be a collection lens, collects the multi-chromatic light rays 260 that have the angle to the imaging axis 250 (e.g., that are parallel to the color sensing axis 255), and focuses the light rays 260 into optical transmission medium 270. In one embodiment, the color sensor has a receptive field of 2 mm round, the optical transmission medium 270 has a fiber core with a diameter of 100 µm, and the lens 264 has a ½₀ magnification. In one example embodiment, the optical path from the lens to the imaged object is around 80 mm. Accordingly, in such an example the focal length of the lens is about F=4 mm. The lens diameter will determine the amount of collected light. In one embodiment, the lens has an aperture of about 2 mm to 3 mm. The optical transmission medium 270 then directs the light rays 260 into color sensor 275. The optical transmission medium 270 with the lens 264 allows the passing of light rays from the optical path of the optical scanning system 230 into the color sensor 275, which may be positioned at any convenient location in the imaging apparatus 197.

Spectrometers are usually large devices that cannot be fit within tight spatial constraints. Use of the optical transmission medium 270 may alleviate size constraints of the color sensor by enabling it to be placed away from the probe 200. One end of the optical transmission medium (e.g., the end that includes lens 264) may be placed near the optical path of the optical scanning system 230, but the color sensor 275 may be placed distant from the optical path of the optical scanning system 230. Additionally, use of the optical transmission medium 270 may allow for a less constrained optical design of a lens and optics of the color sensor 275. Notably, the lens 264, optical transmission medium 270 and color sensor 275 are outside of the optical path of the optical scanning system 230 (e.g., outside of the optical path of a detector that generates 3D images of the tooth 210). Additionally, no beam splitter or mirror is used to direct the light rays 260 into the lens 264. Additionally, in some embodiments the color sensor 275 is positioned near the optical path of the detector and directly receives rays of multi-chromatic light. In such embodiments, the optical transmission medium or other optical transmission medium may be omitted.

By knowing the exact relation between optical scanning system (scanning optics) and the color sensor's 275 optics, it is possible to accurately determine the path of the light entering the color sensor 275 in relation to the light entering the optical scanning system 230. The imaging device 197 can determine the 3D shape of the tooth 210 (or other scanned object) using the optical scanning system 230. By combining the 3D shape and the known relation between the optics, it is possible to determine the exact position in space which is sampled by the color sensor 275. The optical path of the optical scanning system 230 and the light path of the color sensor need not be the same as long as they overlap over the scanned object.

In one embodiment, the optical transmission medium 270 may be omitted. In such an embodiment, the color sensor 275 may be placed near to, and outside of, the optical path of the optical scanning system 230. The lens 264 may be placed in front of the color sensor 275, and may focus rays into the color sensor 275. The lens 264 and/or color sensor 275 may be oriented at an oblique angle to the imaging axis 250 such that the color sensing axis 255 is at the oblique angle to the imaging axis 250. Notably, no beam splitter or mirror is used to direct the light rays 260 into the color sensor 275 in this embodiment.

FIG. 2C illustrates an alternative design for an imaging apparatus 199 with a color sensor 275. In some embodiments, as shown in FIG. 2C, the color sensing axis 255 (e.g., the optical path of the color sensor's optics) is parallel to the imaging axis 250 (e.g., the optical path of the optical scanning system 230). To enable the color sensing axis 255 to be parallel to the imaging axis 250, a beam splitter 276 is placed in the optical path of the optical scanning system 230. The beam splitter 276 may be a relatively small beam splitter that only occupies a small portion of the FOV of the optical scanning system 230. For example, the beam splitter may be a few square millimeters. The beam splitter 276 may pass 100% of light rays at the wavelength (or wavelengths) used by optical scanning system 230, but may reflect up to 50% of the energy of wavelengths of light used by color sensor 275. In one embodiment, the beam splitter reflects 10-30% of the energy of the wavelengths used by color sensor (e.g., wavelengths at the visible spectrum) and passes 70-90% of the energy. The passed light rays may be received by optical scanning system 230 to generate a color 2D image.

Figure 3:
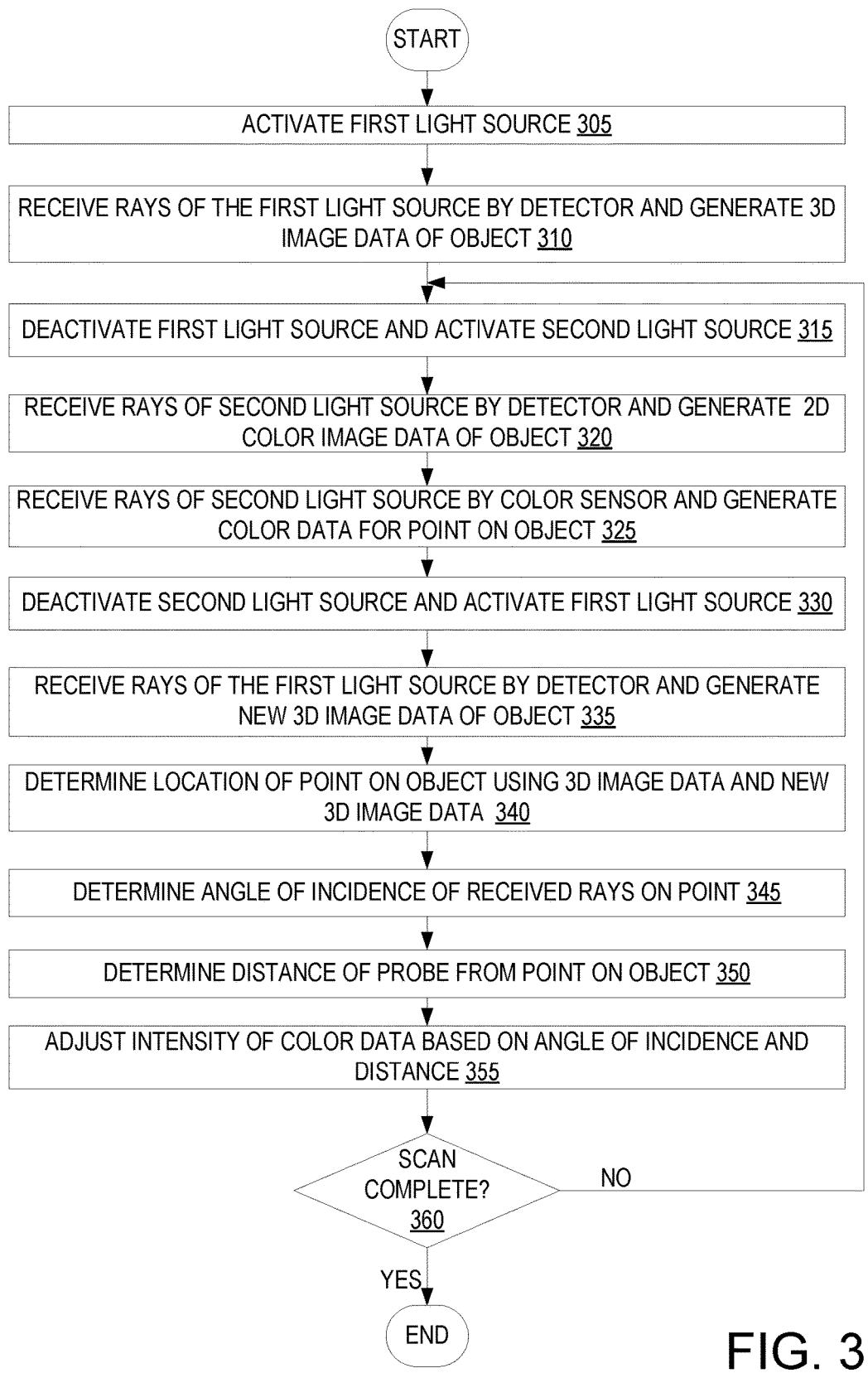
FIG. 3 is a flow chart showing one embodiment of a method for generating three dimensional image data and color data by an imaging apparatus.

FIG. 3 is a flow chart showing one embodiment of a method 300 for generating three dimensional image data and color data by an imaging apparatus. Method 300 may be performed by processing logic that may comprise hardware (e.g., circuitry, dedicated logic, programmable logic, microcode, etc.), software, or a combination thereof. In one embodiment, at least some operations of method 300 are performed by a computing device (e.g., computing device 24 of FIG. 1B). In one embodiment, at least some operations of method 300 are performed by an imaging apparatus (e.g., imaging apparatus 20 of FIG. 1A).

At block 305 of method 300, processing logic activates a first light source. The first light source may be a laser that generates coherent light. In one embodiment, the first light source emits a coherent light beam that is split into an array of light rays. At block 310, a detector of an imaging apparatus receives rays of the first light source and 2D image data of an object that the rays have reflected off of at multiple different focus settings. This 2D image data is usable to generate a 3D image of the object.

At block 315, processing logic deactivates the first light source and activates a second light source. The second light source may be a multi-chromatic light source (e.g., a light source that generates white light). The second light source may generate incoherent light. At block 320, the detector of the imaging apparatus receives rays of the second light source that have been scattered off of the object and generates a 2D color image of the object. At block 325, a color sensor (e.g., hyper spectral sensor or colorimeter) of the imaging apparatus receives one or more rays of the second light source and generates color data for a spot on the object that the one or more rays have been scattered from.

At block 330, processing logic deactivates the second light source and reactivates the first light source. At block 335, the detector receives additional rays of the first light source that have reflected off of the object and generates new 3D image data of the object.

At block 340, processing logic determines a location of the spot on the object for which color data was generated using the 3D image data generated at block 310 and the additional 3D image data generated at block 325. The location of a receptive field of the color sensor within a larger FOV of the detector may be known. Accordingly, the location of the receptive field of the color sensor within the first 3D image data and the location of the receptive field of the color sensor within the additional 3D image data may be determined. The location of the spot on the object may then be determined by interpolating between the location of the receptive field of the color sensor within the first 3D image data and the location of the receptive field of the color sensor within the additional 3D image data.

In one embodiment the location of the receptive field of the color sensor is interpolated using image data from two or more consecutive 3D scans. These 3D scans are registered with one another (stitched together) using, for example, an iterative closest point (ICP) algorithm. This provides the relative probe position as a function of time. A motion trajectory can be estimated from the changing relative position of the probe as a function of time. The time at which the spectral measurement (color measurement) was generated between two consecutive 3D scans may be determined or estimated (e.g., estimated as a time equidistant from the times of the first 3D scan taken prior to the spectral measurement and the second 3D scan taken after the spectral measurement). The relative position in the time of the spectral measurement is computed from the trajectory. The position of the receptive field position and direction vector in the time of the spectral measurement is computed. The point on the 3D object that intersects with the direction vector that represents the direction of rays of light in the receptive field may then be computed.

At block 345, an angle of incidence of the received rays of the second light source on the spot are determined based on a known trajectory of the rays and the 3D shape of the object at the spot. At block 350, a distance of the spot from a probe of the imaging apparatus is determined. At block 355, an intensity of the color data is adjusted based on the angle of incidence and the distance. The intensity and/or other parameters of the color data may also be adjusted based on other normalization factors as discussed above.

Repeated measurements of the same region will be (a) normalized and then (b) weighted and normalized according to the weighting. As set forth above, different angles have different intensity. For small angles, the relationship of diffused model will be used for normalization. Small angles are preferred over large angles. Any angles of incidence that are larger than a threshold angle will be discarded. Otherwise, the intensity will be weighted according to angle. Different regions of the FOV and different distances offer different illumination power. These parameters are used for normalization as well. Additionally, there is a range of angles for which spectral reflection will occur. Spectral reflectance occurs when the angle from the surface normal to an illumination source (e.g., to second light source) and the angle of the incidence at the spot (receptive field of the color sensor) are identical and opposite. Color measurements at these angles may also be discarded.

At block 360, processing logic determines whether a scan is complete. If the scan is not complete, then the process returns to block 315, and the first light source is again deactivated and the second light source is again activated. The method then repeats blocks 320-355. At the reiteration of block 340, a new spot on the object may be determined using the 3D image data generated at the first iteration of block 335 and the additional 3D image data generated at the second iteration of block 335. If at block 360 a determination is made that the scan is complete, then the method ends.

Figure 4:
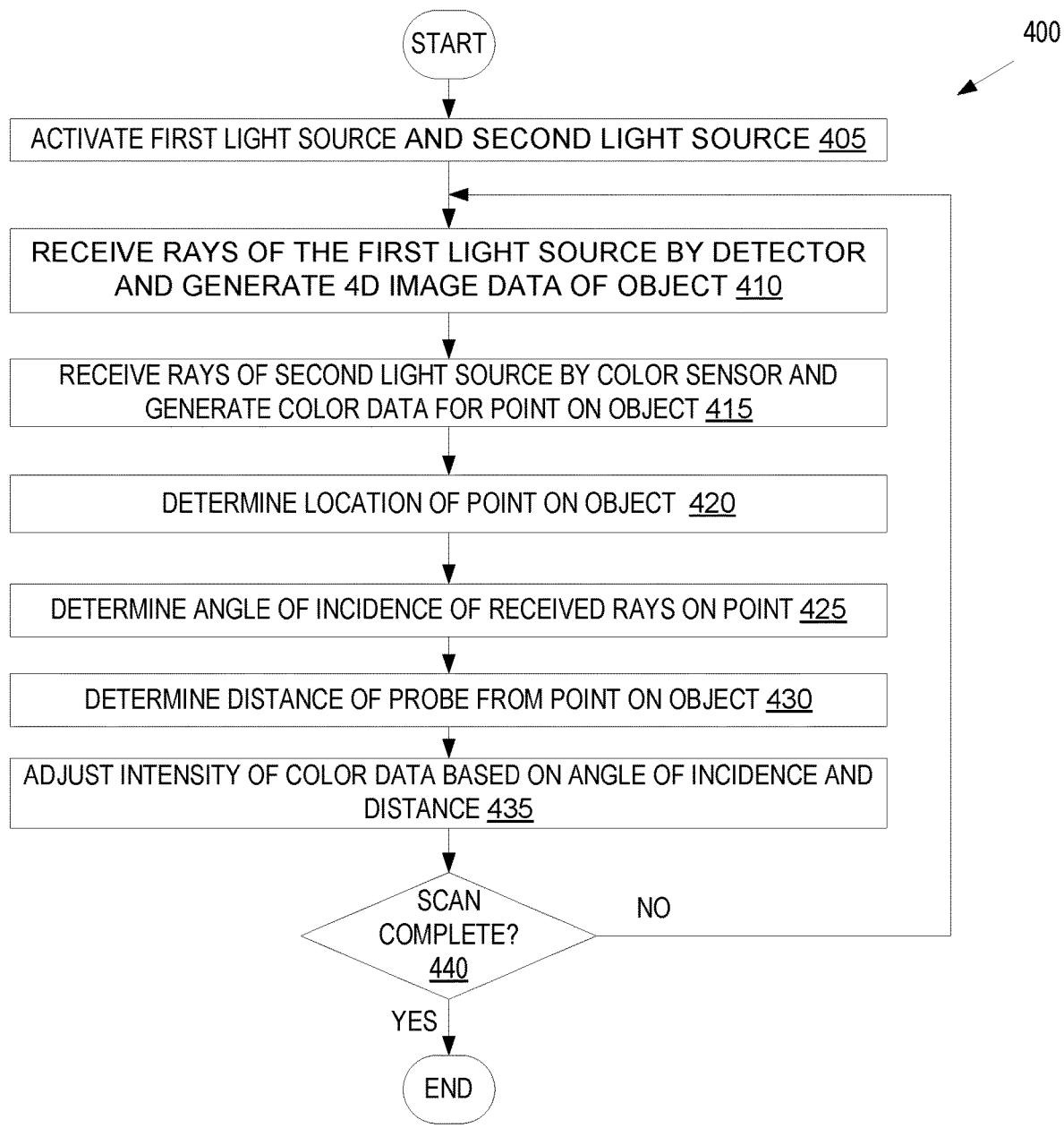
FIG. 4 is a flow chart showing another embodiment of a method for generating three dimensional image data and color data by an imaging apparatus.

FIG. 4 is a flow chart showing another embodiment of a method 400 for generating three dimensional image data and color data by an imaging apparatus. Method 400 may be performed by processing logic that may comprise hardware (e.g., circuitry, dedicated logic, programmable logic, microcode, etc.), software, or a combination thereof. In one embodiment, at least some operations of method 400 are performed by a computing device (e.g., computing device 24 of FIG. 1B). In one embodiment, at least some operations of method 400 are performed by an imaging apparatus (e.g., imaging apparatus 20 of FIG. 1A).

At block 405 of method 400, processing logic activates a first light source and a second light source. The first light source may be a laser that generates coherent light. In one embodiment, the first light source emits a coherent light beam that is split into an array of light rays. The second light source may be a multi-chromatic light source (e.g., a light source that generates white light). The second light source may generate incoherent light.

At block 410, a detector of an imaging apparatus receives rays of the first light source and generates 3D image data of an object that the rays have reflected off of. A filter in an optical path of the detector may filter out rays of the second light source so that the rays of the second light source do not reach the detector.

At block 415, a color sensor (e.g., hyper spectral sensor or colorimeter) of the imaging apparatus receives one or more rays of the second light source and generates color data for a spot on the object that the one or more rays have been reflected from. The rays of the second light source may have an oblique angle to the optical path of the detector and to an imaging axis of the detector. Accordingly, the rays of the second light source may exit the optical path of the detector without any additional optics to redirect the rays of the second light source.

At block 420, processing logic determines a location of the spot on the object for which color data was generated using the 3D image data generated at block 410. The location of a receptive field of the color sensor within a larger FOV of the detector may be known. Accordingly, the location of the receptive field of the color sensor within the 3D image data may be determined since the 3D image data and the color data is generated in parallel.

At block 425, an angle of incidence of the received rays of the second light source on the spot are determined based on a known trajectory of the rays and the 3D shape of the object at the spot. At block 430, a distance of the spot from a probe of the imaging apparatus is determined. At block 435, an intensity of the color data is adjusted based on the angle of incidence and the distance. The intensity and/or other parameters of the color data may also be adjusted based on other normalization factors as discussed above. Accordingly, when a uniform region is captured (e.g., a receptive field or spot of the color sensor is fully on a single tooth), the surface captured may be connected to a spectrum at a specific distance and angle.

Repeated measurements of the same region will be (a) normalized and then (b) weighted and/or summed (e.g., with a weighted sum) and normalized according to the weighting. As set forth above, different angles have different intensity. For small angles, the relationship of diffused model will be used for normalization. Small angles are preferred over large angles. Any angles of incidence that are larger than a threshold angle will be discarded. Otherwise, the intensity will be weighted according to angle. Different regions of the FOV and different distances offer different illumination power. These parameters are used for normalization as well. Additionally, there is a range of angles for which spectral reflection will occur. Spectral reflectance occurs when the angle from the surface normal to an illumination source (e.g., to second light source) and the angle of the incidence at the spot (receptive field of the color sensor) are identical and opposite. Color measurements at these angles may also be discarded.

At block 440, processing logic determines whether a scan is complete. If the scan is not complete, then the process returns to block 410. If at block 440 a determination is made that the scan is complete, then the method ends.

Figure 5:
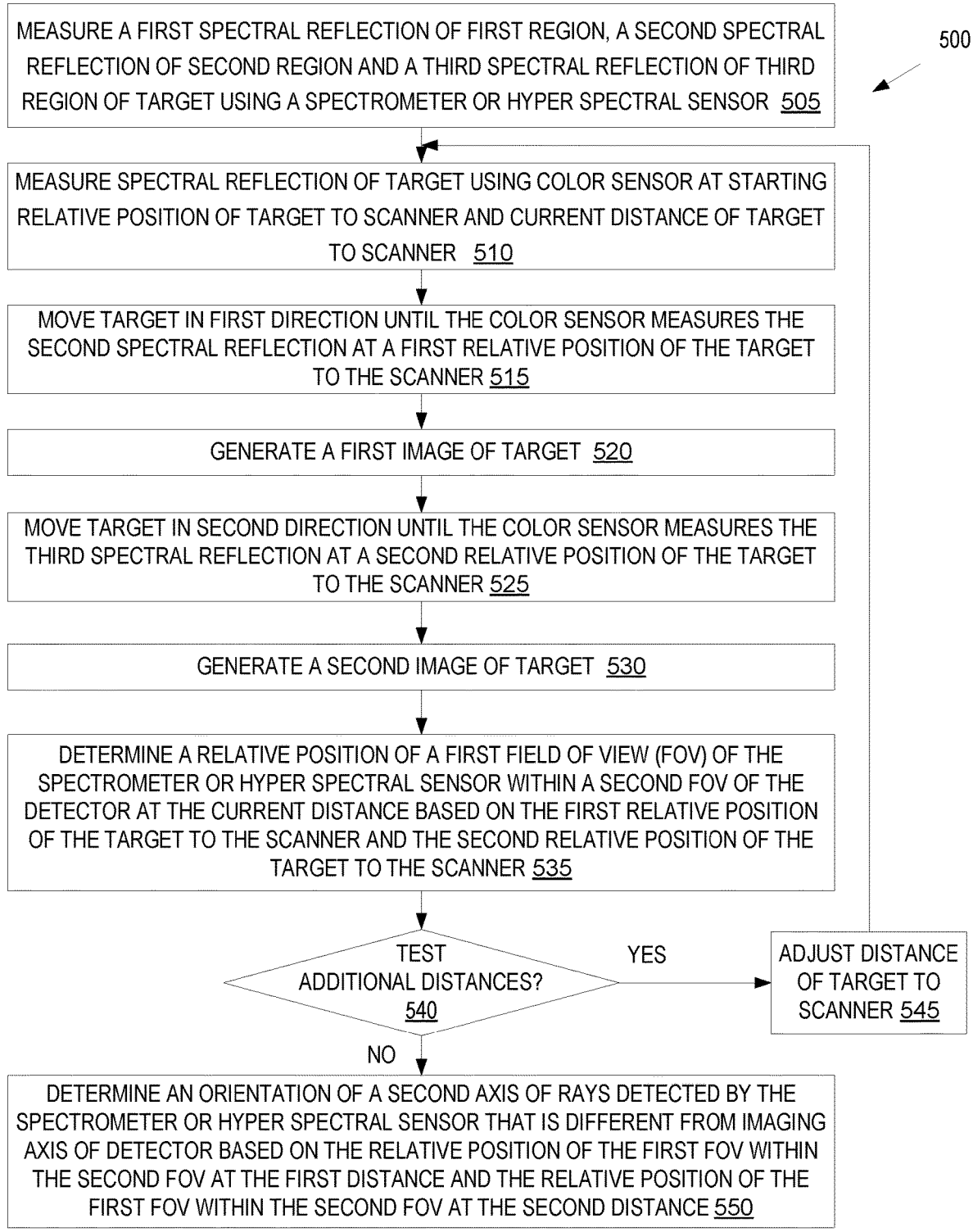
FIG. 5 is a flow chart showing one embodiment of a method for calibrating a color sensor to a detector of an imaging apparatus.

FIG. 5 is a flow chart showing one embodiment of a method 500 for calibrating a color sensor to a detector of an imaging apparatus. Method 500 may be performed by processing logic that may comprise hardware (e.g., circuitry, dedicated logic, programmable logic, microcode, etc.), software, or a combination thereof. In one embodiment, at least some operations of method 500 are performed by a computing device (e.g., computing device 24 of FIG. 1B). In one embodiment, at least some operations of method 500 are performed by an imaging apparatus (e.g., imaging apparatus 20 of FIG. 1A). Method 500 may be performed after color 2D images (e.g., view finder images) have been calibrated with 3D images, where the color 2D images and 3D images may be generated using the same detector or using different detectors. These images may be calibrated by generating a color 2D image of a target at a relative position of a probe of the imaging apparatus to the target and generating a 3D image of the target at the relative position of the probe to the target. The two images may then be registered, and an offset (if any) may be determined between the two images. Calibration of the color sensor to the imaging apparatus may include determining a size, position, shape and/or direction of a receptive field of the color sensor within a larger FOV of the detector. The receptive field of the color sensor is essentially a spot. The color sensor is not a camera imaging system, and so it is not possible to calibrate the color sensor by finding an image to register to.

At block 505 of method 500, multiple regions on a specialized target are measured for spectral reflectance (e.g., for color). The target may include a first region having a first spectral reflectance, a second region having a second spectral reflectance and a third region having a third spectral reflectance. The first region may be a background region, and may have a spectral reflection for black, white, or a well known color. In one embodiment, the second spectral reflectance is for green and the third spectral reflectance is for blue. The second region may be offset from the first region in a first direction. The third region may be offset from the first region in a second direction that is orthogonal to the first direction. For example, the target may have a background color, at least one vertical patch of a first color, and at least one horizontal patch of a second color. The spectral reflectances of the various regions on the target may be measured using a color sensor (e.g., a hyper spectral sensor or colorimeter) of an imaging apparatus (e.g., of an intraoral scanner).

At block 510, the target is positioned in front of a probe of the imaging apparatus at a first distance from the probe and at a first relative position (e.g., x and y position) of the target to the probe so that the first region of the target is in a receptive field of the color sensor. The spectral reflectance at the starting relative position is measured to verify that the first region is in the receptive field of the color sensor.

At block 515, the target is moved in the first direction (e.g., horizontally) until the color sensor measures the second spectral reflection at a first relative position of the target to the probe. At block 520, a first image of the target is generated by the detector. In one embodiment, the detector generates both a 3D image of the target at the first relative position of the target to the probe and generates a 2D image (e.g., a view finder image) of the target at the first relative position of the target to the probe.

At block 525, the target is moved in the second direction (e.g., vertically) until the color sensor measures the third spectral reflection at a second relative position of the target to the probe. At block 530, a second image of the target is generated by the detector. In one embodiment, the detector generates both a second 3D image of the target at the second relative position of the target to the probe and generates a second 2D image (e.g., a view finder image) of the target at the second relative position of the target to the probe.

FIGS. 6A-E are figures showing calibration of a color sensor to a detector of an imaging apparatus. Each of FIGS. 6A-E show a FOV 605 of the detector of the imaging apparatus and the receptive field 610 of the color sensor within the FOV 605 of the detector. The first FOV 605 may have a size of about 14×18 mm in some embodiments. The receptive field 610 may have a diameter of about 1-2 mm in some embodiments. Also shown are various relative positions of a target 612 within the FOV 605 of the detector. The target includes a first region 615 having a first spectral reflectance, a second region 620 having a second spectral reflectance, and a third region 625 having a third spectral reflectance. As shown, the first, second and third regions are considerably larger than the size of the receptive field 610 that has an unknown position. In one embodiment, it is assumed that a material type of the target is fully diffusive so that exact angles of view will not affect the spectral reflectance measurements.

FIG. 6A corresponds to the starting relative position of the target to the probe at block 510. FIG. 6B shows the first relative position of the target to the probe at block 520 after the target has been moved horizontally in the first direction and the color of the second region is detected. As shown, the receptive field 610 includes an edge of the second region 620. FIG. 6C shows an additional relative position of the target to the probe after the target has been moved further in the first direction (e.g., in the horizontal direction).

FIG. 6D shows the second relative position of the target to the probe at block 530 after the target has been moved vertically in the second direction and the color of the third region is detected. As shown, the receptive field 610 includes an edge of the third region 625. FIG. 6E shows an additional relative position of the target to the probe after the target has been moved further in the second direction (e.g., in the vertical direction).

Figure 7A:
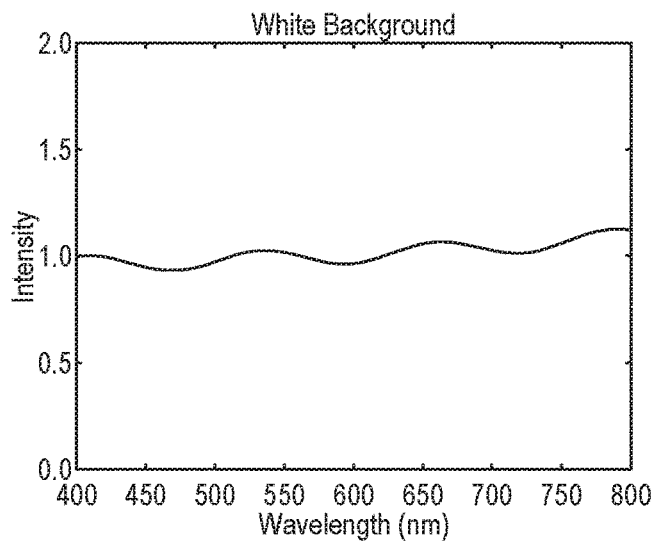
FIGS. 7A-C are color spectrum graphs of various regions of a calibration target.
Figure 7B:
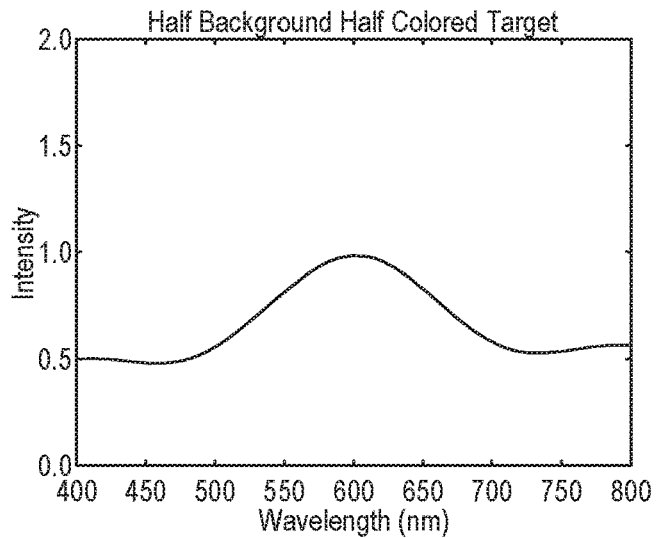
Figure 7C:
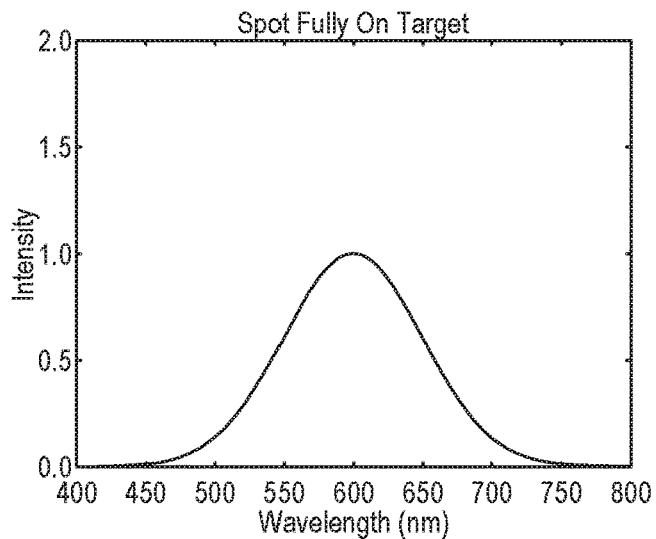

FIGS. 7A-C are color spectrum graphs of various regions of a calibration target (e.g., of the target 612 of FIGS. 6A-E). FIG. 7A shows the spectral reflectance of the first region (in this case a white region) as measured at the initial relative position shown in FIG. 6A. FIG. 7B shows the spectral reflectance measured at the second relative position shown in FIG. 6B, where the receptive field 610 is partly on the second region 620 and partly on the first region 615. A mixture of two spectrums can be seen in FIG. 7B. FIG. 7C shows the spectral reflectance measured at the relative position shown in FIG. 6C, where the receptive field 610 is completely on the second region 620.

Referring back to FIG. 5, at block 535 a relative position of the receptive field 610 of the color sensor within the FOV 605 of the detector at the first distance is determined based on the first relative position of the target to the probe and the second relative position of the target to the probe. The spectral reflectance at the interface of the first region to the second region may be determined according to the equation:

$$S_{mixed}(w) = S_{color1}(w) \cdot \alpha + S_{color1}(w) \cdot (1-\alpha)$$

Where $S_{mixed}(w)$ represents the mixed spectral reflectance, $S_{color1}(w)$ represents the spectral reflectance from the first region, and the $S_{color2}(w)$ represents the spectral reflectance of the second region, and α is the alpha value. Processing logic may minimize α so that Sum($|S_{mixed}(w) - S_{measured}|$) is minimized, where $S_{measured}$ is the spectral reflectance that is measured at a given relative position of the target to the probe.

Plotting α as a function of position will give the shape of the one dimensional integral of the receptive field 610 in the first direction. Similar computations may be made of the second direction.

The spectral reflectance at the interface of the first region to the third region (or the second region to the third region) may be determined according to the equation:

$$S_{mixed}(p) = S_{color1}(p) \cdot \alpha + S_{color3}(p) \cdot (1-\alpha)$$

Where $S_{mixed}(p)$ represents the mixed spectral reflectance, $S_{color1}(p)$ represents the spectral reflectance from the first region, and the $S_{color3}(p)$ represents the spectral reflectance of the second region, and α is the alpha value. Processing logic may minimize α so that Sum($|S_{mixed}(p) - S_{measured}|$) is minimized, where $S_{measured}$ is the spectral reflectance that is measured at a given relative position of the target to the probe.

Again plotting α as a function of position will give the shape of the one dimensional integral of the receptive field 610 in the second direction. Assuming a separable function, FOV(x,y)=Fx(x)·Fy(y) can give a full distribution function for the receptive field 610 (also referred to a full spot distribution function), where FOV(x,y) is the receptive field sensitivity. The receptive field sensitivity may be used when doing a weighted sum when the receptive field is on the border of two regions of the target.

Figure 7D:
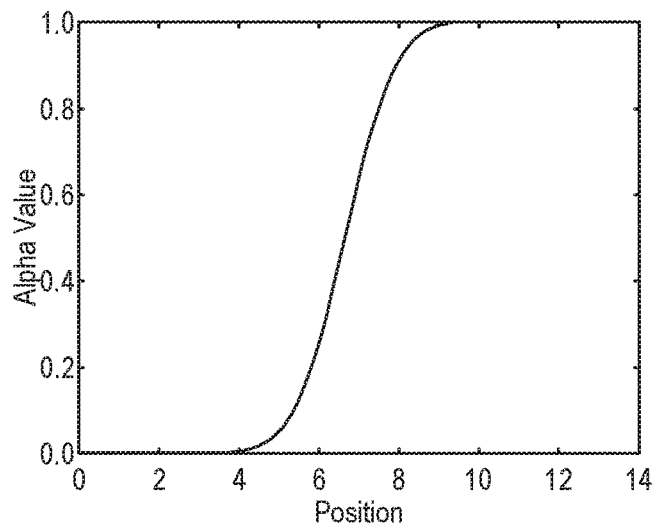
FIG. 7D is a graph of alpha value verses position of a calibration target.

FIG. 7D is a graph of alpha value verses position of a calibration target. The highest derivative position will point to the position of the center and identify the location of the receptive field 610 in the first direction and/or second direction. Accordingly, the x and y coordinates of the center of the receptive field 610 within the FOV 605 may be determined at block 535.

Returning to FIG. 5, at block 540 processing logic determines whether additional distances of the target to the probe are to be tested. In some embodiments, the axis and optical path for the color sensor have an oblique angle to the imaging axis and optical path of the detector used to generate 3D images. Accordingly, the spot position (position of the receptive field) of the color sensor will change with changes in distance of an object to the probe. In such embodiments additional distances should be tested to generate a vector that is usable to determine the spot location at each object distance. If an additional distance is to be tested, the method proceeds to block 545, and a distance of the target to the probe is adjusted. For example, the target may be moved 1-10 mm in depth (z direction). The operations of blocks 510-535 are then repeated at the new depth. The center of the receptive field of the color sensor will change linearly with changes in Z. Accordingly, two depths are sufficient to generate a three dimensional vector that indicates the x,y,z position of the center of the receptive field of the color sensor. Additional distances may be tested to increase accuracy however.

Figure 7E:
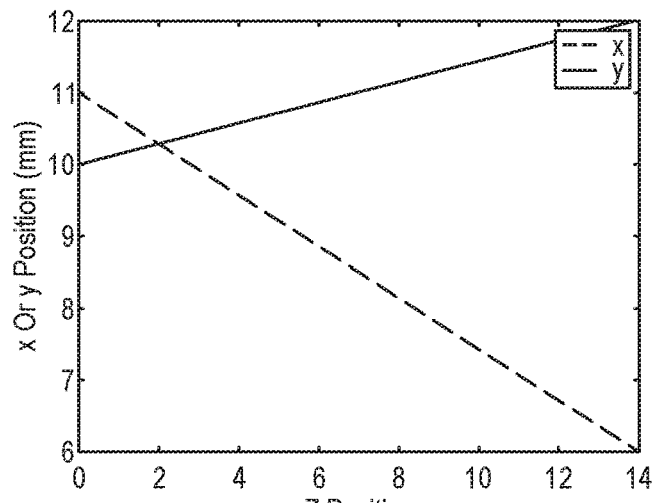
FIG. 7E is a graph of a receptive field position of a color sensor as a function of depth.

At block 550, an orientation of a second axis of rays detected by the color sensor that is different from the imaging axis of the detector is determined based on the relative position of the receptive field within the FOV at the first distance and the relative position of the receptive field within the FOV at the second distance. FIG. 7E is a graph of a receptive field position of a color sensor as a function of depth. The angles of the x and y lines in FIG. 7E imply the angles of the 3D rays of the receptive field of the color sensor (the spot). As the Z position of the target and X,Y positions of the regions are also scanned (e.g., 2D and 3D images are generated), these angles will provide the spot direction relative to the 3D coordinate system of the imaging device.

Figure 7F:
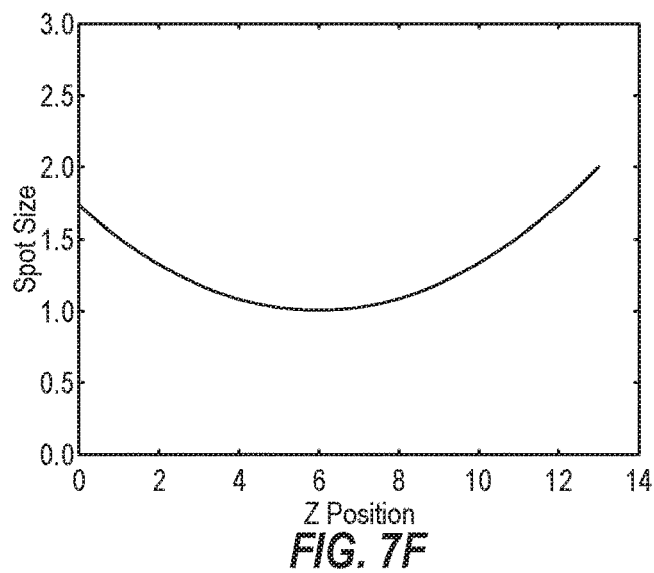
FIG. 7F is a graph of receptive field size of a color sensor as a function of depth.

The spot size (size of the receptive field) of the color sensor can also change with changes in depth. The best focus position is the position that has the smallest spot size. The nearest and furthest distances will have the largest spot sizes. Repeated spot size measurements in different depth settings of the target (different Z values) may create the chart shown in FIG. 7F. FIG. 7F is a graph of receptive field size of a color sensor as a function of depth.

Accordingly, as a result of calibration the position and angles of the spot are known as a function of distance, and a size of the spot is also known as a function of distance. Additional calibration may also be performed of the color sensor, such as a calibration for stray light level and offsets. In one embodiment, a color measurement is performed by the color sensor with no illumination in a dark environment. This color measurement may then be subtracted from each future color measurement. Additionally, a measurement of air (no target) may be taken using each available illumination source (e.g., with the second light source turned on but no target or object in the FOV of the probe). This will measure a stray light level and offsets for each wavelength of the color sensor. These values may also be subtracted from each color measurement generated, depending on the light source used for the color measurement. For example, the measurement of air using the second light source may be subtracted from each future color measurement that also uses the second light source. Additionally, the spectral responses of each of the regions of the target may be measured for one or more illumination sources. By analyzing the spectral response of the different colored regions and different illumination sources, processing logic can determine the spectral intensity of each light source multiplied by the color sensor's gains per wavelength as well as color sensor cross talk levels.

At some angles of incidence spectral reflection and/or specular reflection will occur. In one embodiment, calibration is performed to identify the range of angles of incidence for which spectral and/or specular reflection occurs. Specular reflections may later be discarded.

In one embodiment, specular reflection angles are determined using a special target having a shape of a sphere or semi-sphere (e.g., a half ball). The target is composed of a reflective material. The target's three dimensional shape, including a diameter and position of the target, is measured using the detector. Then the multi-chromatic light source is enabled, and points of reflection can be identified in a color 2D image generated by the detector based on detection of the multi-chromatic light that reflects off of the target. From these points of reflection in the 2D image and the known 3D shape of the target, the position of the light sources for the multi-chromatic light in the FOV of the detector can be computed. The position of the light sources can then be used to determine specular reflections.

In an example, the detector may measure a three dimensional shape of a target, the target having a shape of a sphere or semi-sphere and being comprised of a reflective material. One or more multi-chromatic light sources may then be enabled. The detector may measure intensities of light reflected off of a plurality of points on the target. This measurement may be a 2D measurement in embodiments. Processing logic may then identify one or more points of reflection on the target based on the intensities of light reflected off of the plurality of points on the target, wherein those points of the plurality of points having a highest intensity are identified as the one or more points of reflection. Processing logic may then determine a position of each of the one or more multi-chromatic light sources based on the three dimensional shape of the target and the one or more points of reflection (e.g., by computing the angle of incidence at a point of reflection and tracing a ray back to a light source using the angle of incidence). The position of the light sources can then be used to determine specular reflections.

Figure 9:
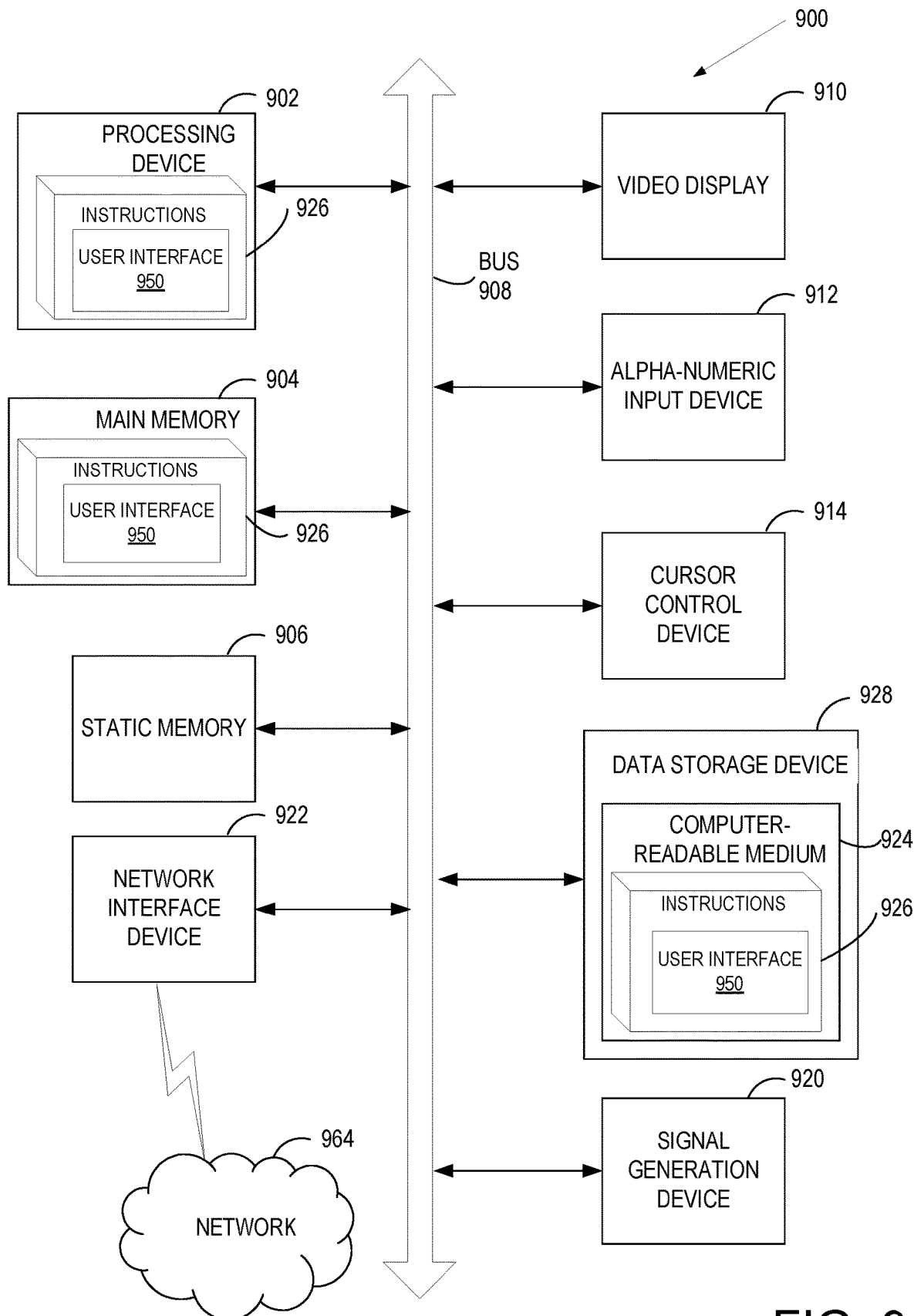
FIG. 9 illustrates a block diagram of an example computing device, in accordance with embodiments of the present invention.

FIG. 9 illustrates a diagrammatic representation of a machine in the example form of a computing device 900 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, computing device 900 corresponds to computing device 24 of FIG. 1B.

The example computing device 900 includes a processing device 902, a main memory 904 (e.g., read-only memory (ROM), flash memory, dynamic random access memory (DRAM) such as synchronous DRAM (SDRAM), etc.), a static memory 906 (e.g., flash memory, static random access memory (SRAM), etc.), and a secondary memory (e.g., a data storage device 928), which communicate with each other via a bus 908.

Processing device 902 represents one or more general-purpose processors such as a microprocessor, central processing unit, or the like. More particularly, the processing device 902 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. Processing device 902 is configured to execute the processing logic (instructions 926) for performing operations and steps discussed herein.

The computing device 900 may further include a network interface device 922 for communicating with a network 964 or other device. The computing device 900 also may include a video display unit 910 (e.g., a liquid crystal display (LCD) or a cathode ray tube (CRT)), an alphanumeric input device 912 (e.g., a keyboard), a cursor control device 914 (e.g., a mouse), and a signal generation device 920 (e.g., a speaker).

The data storage device 928 may include a machine-readable storage medium (or more specifically a non-transitory computer-readable storage medium) 924 on which is stored one or more sets of instructions 926 embodying any one or more of the methodologies or functions described herein. A non-transitory storage medium refers to a storage medium other than a carrier wave. The instructions 926 may also reside, completely or at least partially, within the main memory 904 and/or within the processing device 902 during execution thereof by the computer device 900, the main memory 904 and the processing device 902 also constituting computer-readable storage media.

The computer-readable storage medium 924 may also be used to store a user interface 950, color capturing module and/or color image processing module which may correspond similarly named modules of FIG. 1B. The computer readable storage medium 924 may also store a software library containing methods that call the user interface 950, color capturing module and/or color image processing module. While the computer-readable storage medium 924 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A non-transitory computer readable medium comprising instructions that, when executed by a processing device, cause the processing device to perform operations comprising:

receiving scan data of a tooth during a first mode of operation, the scan data of the tooth having been generated by an intraoral scanner;

invoking a second mode of operation;

presenting, in a graphical user interface (GUI), an image of the tooth;

presenting, in the GUI, indications of a plurality of color zones of the tooth, the indications comprising, for at least one color zone of the plurality of color zones, an indication that insufficient color information has been received, wherein each color zone represents a separate region of the tooth for which an approximately uniform color is to be used; and categorizing, for one or more color zones of the plurality of color zones for which sufficient color information has been received, each of the one or more color zones according to a color pallet used for dental prosthetics.

2. The non-transitory computer readable medium of claim 1, wherein the scan data comprises three-dimensional (3D) scan data, the operations further comprising:

stitching together a plurality of scans of the tooth from the 3D scan data of the tooth; and generating the image of the tooth based on the plurality of scans of the tooth that have been stitched together.

3. The non-transitory computer readable medium of claim 1, wherein the plurality of color zones comprises one or more color zones for which a color measurement was made during the first mode of operation, and wherein the indications show that the color measurement was made for the one or more color zones.

4. The non-transitory computer readable medium of claim 1, wherein the plurality of color zones comprise at least one of a cervical color zone, a first interproximal color zone on a first side of the tooth, a second interproximal color zone on a second side of the tooth, a body color zone, or an incisal color zone.

5. A non-transitory computer readable medium comprising instructions that, when executed by a processing device, cause the processing device to perform operations comprising:

receiving scan data of a tooth during a first mode of operation, the scan data of the tooth having been generated by an intraoral scanner;

invoking a second mode of operation;

presenting, in a graphical user interface (GUI), an image of the tooth;

presenting, in the GUI, indications of a plurality of color zones of the tooth, the indications comprising, for at least one color zone of the plurality of color zones, an indication that insufficient color information has been received, wherein each color zone represents a separate region of the tooth for which an approximately uniform color is to be used; and presenting, in a view finder, a marker identifying a receptive field of a color sensor of the intraoral scanner, wherein the marker indicates whether a probe of the intraoral scanner is pointed at a region of the tooth associated with the at least one color zone for which insufficient color data has been received.

6. The non-transitory computer readable medium of claim 5, the operations further comprising:

determining whether the probe is positioned for measurement of the region of the tooth associated with the at least one color zone;

responsive to determining that the probe is positioned for measurement of the region of the tooth associated with the at least one color zone, outputting at least one of an audio signal or a video signal; and performing a color measurement of the region of the tooth associated with the at least one color zone.

7. The non-transitory computer readable medium of claim 6, the operations further comprising:

determining that sufficient color information has been obtained for the at least one color zone; and updating the image of the tooth to indicate that color information has been received for the at least one color zone.

8. The non-transitory computer readable medium of claim 7, wherein determining that sufficient color information has been obtained for the at least one color zone comprises:

determining that at least a threshold number of color measurements of the at least one color zone have been performed.

9. The non-transitory computer readable medium of claim 6, the operations further comprising:

determining whether an angle of incidence of light rays output by the probe that reflect off of the region of the tooth that is within the receptive field of the color sensor exceeds a threshold or is within a spectral reflection angle; and responsive to determining that the angle of incidence of the light rays exceeds the threshold or is within the spectral reflection angle, providing feedback to change at least one of an angle or an orientation of the probe.

10. The non-transitory computer readable medium of claim 1, the operations further comprising:

receiving color information for the at least one color zone of the tooth; and generating a three-dimensional (3D) model of the tooth using the scan data and the color information for the at least one color zone.

11. A non-transitory computer readable medium comprising instructions that, when executed by a processing device, cause the processing device to perform operations comprising:

during a first mode of operation:

receiving a first scan of scan data of a tooth generated by an intraoral scanner, the first scan associated with a first portion of the tooth;

determining a first shape of the first portion of the tooth;

determining a first relative position of a probe of the intraoral scanner to the tooth;

receiving color information of a point on the tooth;

receiving a second scan of the scan data, the second scan associated with a second portion of the tooth;

determining a second shape of the second portion of the tooth;
determining a second relative position of the probe of the intraoral scanner to the tooth; and
determining a position of the point on the tooth based on an interpolation between the first relative position of the probe to the tooth and the second relative position of the probe to the tooth;
invoking a second mode of operation;
presenting, in a graphical user interface (GUI), an image of the tooth; and
presenting, in the GUI, indications of a plurality of color zones of the tooth, the indications comprising, for at least one color zone of the plurality of color zones, an indication that insufficient color information has been received, wherein each color zone represents a separate region of the tooth for which an approximately uniform color is to be used.

12. A system comprising:
an intraoral scanner configured to generate scan data of a tooth and to perform color measurements of the tooth; and
a computing device operatively connected to the intraoral scanner, wherein the computing device is to:
receive the scan data of the tooth from the intraoral scanner during a first mode of operation;
receive color information of the tooth based on the color measurements;
invoke a second mode of operation;
present, in a graphical user interface (GUI), an image of the tooth;
present, in the GUI, indications of a plurality of color zones of the tooth, the indications comprising, for at least one color zone of the plurality of color zones, an indication that insufficient color information has been received, wherein each color zone represents a separate region of the tooth for which an approximately uniform color is to be used; and
categorize, for one or more color zones of the plurality of color zones for which sufficient color information has been received, each of the one or more color zones according to a color pallet used for dental prosthetics.

13. The system of claim 12, wherein the computing device is further to:
receive color information for the at least one color zone of the tooth; and
generate a three-dimensional (3D) model of the tooth using the scan data and the color information for the at least one color zone.

14. The system of claim 12, wherein the plurality of color zones comprise at least one of a cervical color zone, a first interproximal color zone on a first side of the tooth, a second interproximal color zone on a second side of the tooth, a body color zone, or an incisal color zone.

15. A system comprising:
an intraoral scanner configured to generate scan data of a tooth and to perform color measurements of the tooth; and
a computing device operatively connected to the intraoral scanner, wherein the computing device is to:
receive the scan data of the tooth from the intraoral scanner during a first mode of operation;
invoke a second mode of operation;
present, in a graphical user interface (GUI), an image of the tooth;
present, in the GUI, indications of a plurality of color zones of the tooth, the indications comprising, for at least one color zone of the plurality of color zones, an indication that insufficient color information has been received, wherein each color zone represents a separate region of the tooth for which an approximately uniform color is to be used; and
present, in a view finder, a marker identifying a receptive field of a color sensor of the intraoral scanner, wherein the marker indicates whether a probe of the intraoral scanner is pointed at a region of the tooth associated with the at least one color zone for which insufficient color data has been received.

16. The system of claim 15, wherein the computing device is further to:
determine whether the probe is positioned for color measurement of the region of the tooth associated with the at least one color zone;
responsive to determining that the probe is positioned for color measurement of the region of the tooth associated with the at least one color zone, output at least one of an audio signal or a video signal; and
cause the intraoral scanner to perform a color measurement of the region of the tooth associated with the at least one color zone.

17. The system of claim 16, wherein the computing device is further to:
determine that sufficient color information has been obtained for the at least one color zone; and
update the image of the tooth to indicate that color information has been received for the at least one color zone.

18. The system of claim 17, wherein determining that sufficient color information has been obtained for the at least one color zone comprises determining that at least a threshold number of color measurements of the at least one color zone have been performed.

19. The system of claim 16, wherein the computing device is further to:
determine whether an angle of incidence of light rays output by the probe that reflect off of the region of the tooth that is within the receptive field of the color sensor exceeds a threshold or is within a spectral reflection angle; and
responsive to determining that the angle of incidence of the light rays exceeds the threshold or is within the spectral reflection angle, provide feedback to change at least one of an angle or an orientation of the probe.

20. A system comprising:
an intraoral scanner configured to generate scan data of a tooth and to perform color measurements of the tooth; and
a computing device operatively connected to the intraoral scanner, wherein the computing device is to:
receive a first scan of the scan data during a first mode of operation, the first scan associated with a first portion of the tooth;
determine a first shape of the first portion of the tooth;
determine a first relative position of a probe of the intraoral scanner to the tooth;
receive color information of a point on the tooth;
receive a second scan of the scan data during the first mode of operation, the second scan associated with a second portion of the tooth;
determine a second shape of the second portion of the tooth;

determine a second relative position of the probe of the intraoral scanner to the tooth;

determine a position of the point on the tooth based on an interpolation between the first relative position of the probe to the tooth and the second relative position of the probe to the tooth;

invoke a second mode of operation;

present, in a graphical user interface (GUI), an image of the tooth; and present, in the GUI, indications of a plurality of color zones of the tooth, the indications comprising, for at least one color zone of the plurality of color zones, an indication that insufficient color information has been received, wherein each color zone represents a separate region of the tooth for which an approximately uniform color is to be used.

21. A method comprising:

receiving, by a computing device, three-dimensional (3D) scan data of a tooth from an intraoral scanner in a first mode of operation;

invoking, by the computing device, a second mode of operation;

identifying a plurality of color zones of the tooth, wherein each color zone indicates a separate region of the tooth that is expected to have approximately uniform color;

determining which color zones of the plurality of color zones are color zones for which sufficient color information has been received and which color zones of the plurality of color zones are color zones for which insufficient color information has been received;

presenting, in a graphical user interface (GUI), an image of the tooth; and presenting, in the GUI, data indicating one or more color zones of the plurality of color zones for which sufficient color information has been received.

22. The method of claim 21, further comprising:

presenting, in the GUI, data indicating one or more additional color zones of the plurality of color zones for which insufficient color information has been received.

23. The method of claim 22, further comprising:

receiving color information for the one or more additional color zones of the tooth; and generating a three-dimensional (3D) model of the tooth using the 3D scan data and the received color information for the one or more additional color zones.

24. The method of claim 21, further comprising:

categorizing one or more color zones of the plurality of color zones for which sufficient color information has been received.

25. The method of claim 24, wherein the categorizing of the one or more color zones for which sufficient color information has been received is performed according to a color pallet used for dental prosthetics.

* * * * *